(12) United States Patent
Li et al.

(10) Patent No.: US 7,297,348 B2
(45) Date of Patent: Nov. 20, 2007

(54) BIODEGRADABLE TRIBLOCK COPOLYMERS, SYNTHESIS METHODS THEREFORE, AND HYDROGELS AND BIOMATERIALS MADE THERE FROM

(75) Inventors: Jun Li, Singapore (SG); Xu Li, Singapore (SG); Xiping Ni, Singapore (SG); Kam W. Leong, Ellicott City, MD (US)

(73) Assignees: Omeros Corporation, Seattle, WA (US); Institute of Materials Research and Engineering, Singapore (SG)

( * ) Notice: Subject to any disclaimer, the term of this patent is extended or adjusted under 35 U.S.C. 154(b) by 338 days.

(21) Appl. No.: 10/624,136

(22) Filed: Jul. 18, 2003

(65) Prior Publication Data

US 2004/0072799 A1 Apr. 15, 2004

Related U.S. Application Data

(60) Provisional application No. 60/439,171, filed on Jan. 10, 2003, provisional application No. 60/397,129, filed on Jul. 19, 2002.

(51) Int. Cl.
*A61K 9/14* (2006.01)
(52) U.S. Cl. ...................... 424/485; 424/486
(58) Field of Classification Search ................ 424/485, 424/425, 426, 424, 486, 501, 497, 493, 489, 424/491
See application file for complete search history.

(56) References Cited

U.S. PATENT DOCUMENTS

| | | | |
|---|---|---|---|
| 4,449,938 A | 5/1984 | Pollak | |
| 4,716,203 A | 12/1987 | Casey et al. | |
| 5,298,410 A | 3/1994 | Phillips et al. | |
| 5,324,718 A | 6/1994 | Loftsson | |
| 5,324,775 A | 6/1994 | Rhee et al. | |
| 5,384,333 A | 1/1995 | Davis et al. | |
| 5,472,954 A | 12/1995 | Loftsson | |
| 5,476,909 A | 12/1995 | Kim et al. | |
| 5,543,158 A | 8/1996 | Gref et al. | |
| 5,565,215 A | 10/1996 | Gref et al. | |
| 5,702,717 A | 12/1997 | Cha et al. | |
| 5,922,340 A | 7/1999 | Berde et al. | |
| 5,939,453 A | 8/1999 | Heller et al. | |
| 5,942,241 A | 8/1999 | Chasin et al. | |
| 5,968,543 A | 10/1999 | Heller et al. | |
| 6,083,534 A | 7/2000 | Wallach et al. | |
| 6,096,303 A | 8/2000 | Fick | |
| 6,331,311 B1 | 12/2001 | Brodbeck et al. | |
| 6,346,274 B1* | 2/2002 | Koll et al. .............. | 424/497 |
| 6,420,432 B2 | 7/2002 | Demopulos et al. | |
| 6,545,097 B2 | 4/2003 | Pinchuk et al. | |
| 2002/0019369 A1 | 2/2002 | Li et al. | |
| 2002/0193812 A1 | 12/2002 | Patel et al. | |
| 2003/0082234 A1 | 5/2003 | Seo et al. | |
| 2003/0087985 A1 | 5/2003 | Hubbell et al. | |
| 2003/0143184 A1 | 7/2003 | Seo et al. | |

FOREIGN PATENT DOCUMENTS

| | | |
|---|---|---|
| EP | 0510356 A1 | 10/1992 |
| WO | WO 95/03357 | 2/1995 |
| WO | WO 95/11924 | 5/1995 |
| WO | WO 00/33885 | 6/2000 |
| WO | WO 00/40962 | 7/2000 |
| WO | WO 00/50007 | 8/2000 |
| WO | WO 00/64977 | 11/2000 |
| WO | WO 01/07067 A2 | 2/2001 |
| WO | WO 01/45742 A1 | 6/2001 |
| WO | WO 02/47731 A2 | 6/2002 |
| WO | WO 02/085337 A1 | 10/2002 |

OTHER PUBLICATIONS

Huh, K.M., et al., "Supramolecular-Structured Hydrogel by Inclusion Complexation of Poly(ethylene Glycol) Grafted Dextran with α-Cyclodextrin," *Polymer Preprints 2001* 42(2):146-146 (2001).

Ooya, T., et al., "Biodegradable Polyrotaxanes Aiming at Biomedical and Pharmaceutical Applications," *Biomedical Polymers and Polymer Therapeutics*, Edited by Chiellini et al., Kluwer Academic/Plenum Publishers, New York, 2001, pp. 75-90.

Song, C.X., et al., "Formulation and characterization of biodegradable nanoparticles for intravascular local drug delivery," *Journal of Controlled Release*, 43:197-212 (1997).

Jeong, B., et al., "Drug release from biodegradable injectable thermosensitive hydrogel of PEG-PLGA-PEG triblock copolymers," *Journal of Controlled Release*, 63:155-163 (2000).

Watanabe, J., et al., "Effect of acetylation of biodegradable polyrotaxanes on its supramolecular dissociation via terminal ester hydrolysis," *J. Biomater. Sci. Polymer Edn.*, 10(12):1275-1288 (1999).

Yui, N., et al., "Effect of Biodegradable Polyrotaxanes on Platelet Activation," *Bioconjugate Chem.*, 9:118-125 (1998).

(Continued)

*Primary Examiner*—Michael G. Hartley
*Assistant Examiner*—J Rogers
(74) *Attorney, Agent, or Firm*—Marcia S. Kelbon

(57) ABSTRACT

A drug delivery system that includes a hydrogel formed from cyclodextrin and an amphiphilic copolymer that includes an A polymer block comprising a poly(alkylene oxide) and a B polymer block comprising a poly(hydroxyalkanoate), and a therapeutically effective amount of at least one therapeutic agent intimately contained within the hydrogel. In one preferred embodiment of the invention, the A polymer block is poly(ethylene oxide) (PEO) and the B polymer block is poly[(R)-3-hydroxybutyrate] (PHB), and the copolymer is the triblock ABA copolymer PEO-PHB-PEO. A method of synthesizing the amphiphilic triblock copolymer is also provided.

9 Claims, 24 Drawing Sheets

OTHER PUBLICATIONS

Ooya, T., et al., "Regulation of intracellular metabolism by biodegradable polyrotaxanes," *J. Biomater. Sci. Polymer Edn.*, 9(4):313-326 (1998).

Ooya, T., et al., "Synthesis and characterization of biodegradable polyrotaxane as a novel supramolecular-structured drug carrier," *J. Biomater. Sci. Polymer Edn.*, 8(6):437-455 (1997).

Ooya, T., et al., "Synthesis of theophylline-polyrotaxane conjugates and their drug release via supramolecular dissociation," *Journal of Controlled Release*, 58:251-269 (1999).

Ooya, T., et al., "Polyrotaxanes: Synthesis, Stucture, and Potential in Drug Delivery," *Critical Reviews in Therapeutic Drug Carrier Systems*, 16(3):289-330 (1999).

Doi, Y., "Microbial Polyesters," *VCH Publishers, Inc.*, pp. 99-106 (1990).

Bailey. Jr., F.E., et al., "Poly(ethylene oxide)," Academic Press, Inc., pp. 105-141 (1976).

Bae, Y.H., et al., "Biodegradable amphiphilic multiblock copolymers and their implications for biomedical applications," *Journal of Contorlled Release*, 64:3-13 (2000).

Bromberg, L.E., et al., "Temperature-responsive gels and thermogelling polymer matrices for protein and peptide delivery," *Advanced Drug Delivery Reviews*. 31:197-221 (1998).

Herold, D., et al., "Oxidation of Polyethylene Glycols by Alcohol Dehydrogenase," *Biochemical Pharmacology*, 38(1):73-76 (1989).

Jeong, B., et al., "Thermosensitive sol-gel reversible hydrogels," *Advanced Drug Delivery Reviews*, 54:37-51 (2002).

Kissel, T., et al., "ABA-triblock copolymers from biodegradable polyester A-blocks and hydrophilic poly(ethylene oxide) B-blocks as a candidate for in situ forming hydrogel delivery systems for proteins," *Advanced Drug Delivery Reviews*, 54:99-134 (2002).

Jenekhe, S.A., et al., "Self-Assembly of Ordered Microporous Materials from Rod-Coil Block Copolymers," *Science*, 283:372-375 (Jan. 15, 1999).

Kukula, H., et al., "The Formation of Polymer Vesicles or "Peptosomes" by Polybutadiene-*block*-poly(L-glutamate)s in Dilute Aqueous Solution," *J. Am. Chem. Soc*, 124(8):1658-1663 (2002).

Jeong, B., et al., "Biodegradable block copolymers as injectable drug-delivery systems," *Nature*, 388:860-862 (Aug. 28, 1997).

Van Hest, J.C.M., et al., "Polystyrene-Dendrimer Amphiphilic Block Copolymers with a Generation-Dependent Aggregation," *Science*, 268:1592-1595 (Jun. 16, 1995).

Förster, S., et al., "Amphiphilic Block Copolymers in Structure-Controlled Nanomaterial Hybrids," *Advanced Materials*, 10(3):195-217 (1998).

Alexandridis, P., et al., "Poly(ethylene oxide)-poly(propylene oxide)-poly(ethylene oxide) block copolymer surfactants in aqueous solutions and at interfaces: thermodynamics, structure, dynamics, and modeling," *Physiochemical and Engineering Aspects*, 96:1-46 (1995).

Hirt, T.D., et al., "Telechelic diols from poly[(*R*)-3-hydroxybutyric acid] and poly{[(R)-3-hydroxybutyric acid]-*co*-[(*R*)-3-hydroxyvaleric acid]}," *Macromol. Chem. Phys.*, 197:1609-1614 (1996).

Jeong, B., et al., "Thermoreversible Gelation of PEG-PLGA-PEG Triblock Copolymer Aqueous Solutions," *Macromolecules*, 32:7064-7069 (1999).

Alexandridis, P., "Amphiphilic copolymers and their applications," *Current Opinion in Colloid and Interface Science*, 1:490-501 (1996).

Shuai, X., et al., "Formation of Inclusion Complexes of Poly(3-hydroxybutyrate)s with Cyclodextrins. 1. Immobilization of Atactic Poly(*R,S*-3-hydroxybutyrate) and Miscibility Enhancement between Poly(*R,S*-3-hydroxybutyrate) and Poly(ε-caprolactone)," *Macromolecules*, 35:3126-3132 (2002).

Shuai, X., et al., Stereoselectivity in the Formation of Crystalline Inclusion Complexes of Poly (3-hydroxybutyrate)s with Cyclodextrins, *Macromolecules*, 35:3778-3780 (2002).

Shuai, X., et al., "Inclusion Complex Formation between α,γ-Cyclodextrins and a Triblock Copolymer and the Cyclodextrin-Type-Dependent Microphase Structures of Their Coalesced Samples," *Macromolecules*, 35:2401-2405 (2002).

Wei, M., et al., "Manipulation of Nylon-6 Crystal Structures with Its α-Cyclodextrin Inclusion Complex," *Macromolecules*, 35:8039-8044 (2002).

Wei, M., et al., "Compatiblization of Polymers via Coalescence from Their Common Cyclodextrin Inclusion Compounds," *Macromolecules*, 34:4061-4065 (2001).

Kim, I.S., et al., "Thermo-responsive self-assembled polymeric micelles for drug delivery in vitro," *International Journal of Pharmaceutics*, 205:165-172 (2000).

Jeong, Y.I., et al., "Adriamycin release from flower-type polymeric micelle based on star-block copolymer composed of poly(γ-benzyl L-glutamate) as the hydrophobic part and poly(ethylene oxide) as the hydrophilic part," *International Journal of Pharmaceutics*, 188:49-58 (1999).

Kim, S.Y., et al., "Preparation of characterization of biodegradable nanospheres composed of methoxy poly(ethylene glycol) and DL-lactide block copolymer as novel drup carriers," *Journal of Controlled Release*, 56:197-208 (1998).

Li, J., et al., "Sol-Gel Transition during Inclusion Complex Formation between α-Cyclodextrin and High Molecular Weight Poly(ethylene glycol)s in Aqueous Solution," *Polymer Journal*, 26(9):1019-1026 (1994).

Ooya, T., et al., "Synthesis of a biodegradable polymeric supramolecular assembly for drug delivery," *Macromol. Rapid Commun.*, 16:259-263 (1995).

Loftsson, T., "Increasing the cyclodextrin complexation of drugs and drug biovailability through addition of water-soluble polymers," *Pharmazie*, 53:733-740 (1998).

Amiel, C., et al., "New Associating Polymer Systems Involving Water Soluble β-Cyclodextrin Polymers," *J. Inclusion Phen. Mol. Recog.*, 25:61-67 (1996).

Gogolewski, S., et al., "Tissue Response and in vivo degradation of selected polyhydroxyacids : poly;actides (PLA), poly(3-hydroxybutyrate) (PHB), and poly(3-hydrocybutyrate-co-3-hydroxyvalerate (PHB/VA)," *J. Biomed. Mater. Res.*, 27:1135-1148 (1993) (Abstract Only).

Harada, A., et al., "Double-stranded inclusion complexes of cyclodextrin threaded on poly(ethylene glycol)," *Nature*, 370:126-128 (Jul. 14, 1994).

Li, J., et al., Inclusion Complexation and Formation of Polypseudorotaxanes between Poly[(ethylene oxide-*ran*-(propylene oxide)] and Cyclodextrins, *Macromolecules*, 34:8829-8831 (2001).

Li, J., et al., "Formation of Supramolecular Hydrogels Induced by Inclusion Complexation between Pluronics and α-Cyclodextrin," *Macromolecules*, 34:7236-7237 (2001).

Noda, T, et al., "Micelle Formation of Random Copolymers and Sodium 2-(Acrylamido)-2-methylpropanesulfonate and a Nonionic Surfactant Macromonomer in Water as Studied by Flourescence and Dynamic Light Scattering," *Macromolecules*, 33:3694-3704 (2000).

Wilhelm, M., et al., "Poly(styrene-ethylene oxide) Block Copolymer Micelle Formation in Water: A Fluorescence Probe Study," *Macromolecules*, 24:1033-1040 (1991).

BASF, "Pluronic & Tetronic Surfactants," BASF Corporation, Mount Olive, New Jersey, 29 pages (1989).

Leong, K.W., et al., "DNA-polycation nanospheres as non-viral gene delivery vehicles," *Journal of Controlled Resease*, 53:183-193 (1998).

Chen, G., et al., "Graft copolymers that exhibit temperature-induced phase transitions over a wide range of pH," *Nature*, 373:49-52 (Jan. 5, 1999).

Harada, A., et al., "Preparation and Properties of Inclusion Complexes of Poly(ethylene glycol) with α-Cyclodextrin," *Macromolecules*, 26:5698-5703 (1993).

Harada, A., et al., "Preparation and Characterization of Inclusion Complexes of Polyisobutylene with Cyclodextrins," *Macromolecules*, 29:5611-5614 (1996).

Harada, A., et al., "The molecular necklace: a rotaxane containing many threaded α-cyclodextrins," *Nature*, 356:325-327 (Mar. 26, 1992).

Li, J., et al., "Conformational Analysis of Oligomers of (*R*)-3-Hydroxybutanoic Acid in Solutions by $^1$H NMR Spectroscopy," *Bull. Chem. Soc. Jpn.*, 71:1683-1689 (1998).

Li, J., et al., "Conformational Behavior of Methyl (3*R*)-3-{[3'*R*)-3'-Hydroxybutanoyl]oxy} butanoate in Solutions: Effects of Intramolecular Hydrogen Bond," *Bull. Chem. Soc, Jpn.*, 70:1887-1893 (1997).

* cited by examiner (a) – M-PEO-A (*Mn* 4740)

(b) – PHB-diol (*Mn* 3220)

(c) – PEO-PHB-PEO
  (5000-3800-5000)

(a) α-CD (b) α-CD complexed with PEO-PHB-PEO(2000-5200-2000)

BIODEGRADABLE TRIBLOCK COPOLYMERS, SYNTHESIS METHODS THEREFORE, AND HYDROGELS AND BIOMATERIALS MADE THERE FROM

CROSS REFERENCE TO RELATED APPLICATIONS

The present invention claims the benefit of the filing dates of U.S. Provisional Application No. 60/397,129, filed Jul. 19, 2002 and U.S. Provisional Application No. 60/439,171, filed Jan. 10, 2003.

FIELD OF THE INVENTION

The present invention relates to methods of synthesizing amphiphilic copolymers having poly(hydroxyalkanoate) polymer blocks and poly(alkylene oxide) polymer blocks, hydrogels formed by such polymers with cyclodextrin, and biomaterials including injectable hydrogel drug delivery systems based on such polymers and hydrogels.

BACKGROUND OF THE INVENTION

Many drugs are compounded for delivery by methods that result in a therapeutic effect in the body of a human or other mammal that varies considerably over time. Drugs delivered by intravenous routes may result in a nearly instantaneous peak in blood plasma drug concentration, followed by a gradual decay in blood plasma level as the drug is metabolized. Drugs that are delivered by oral or intramuscular routes may result in a blood plasma concentration of the drug that increases slowly during systemic uptake of the drug, followed by a decrease from peak plasma drug levels. Drug dosing may need to be repeated at frequent intervals, such as daily, but this at best only approximates a continuous or constant therapeutic level.

It would be beneficial to deliver many types of therapeutic agents in a delivery system that provides for sustained release of the agents over an extended period of time. A variety of polymers used for controlled release and delivery of drugs have been developed in the past 20 years. Most of the polymers are formed into implants or injectable microspheres. Such polymers are, and must be, biodegradable and biocompatible. In order to produce suitable forms of polymers, complicated fabrication processes are required that typically involve organic solvents. The use of organic solvents, however, may cause denaturation of some protein drugs, and even traces of an organic solvent may be toxic.

Polymer hydrogels have been explored for drug delivery and controlled release. For example, chemically cross-linked polymer hydrogels have been used as implants. Some injectable drug delivery systems form chemically cross-linked hydrogels in the body after injection, providing a drug depot. However, the chemical reactions occurring in the body due to the presence and/or breakdown of some of these polymers may cause tissue irritation and damage.

Physical polymeric hydrogels have been widely explored for biomaterials applications. Examples include hydrogels formed by complexation of enantiomeric polymer or polypeptide segments, and hydrogels with temperature- or pH-sensitive properties. They attract special attention for controlled drug delivery because of the mild and aqueous conditions involved in trapping delicate bioactive agents such as proteins. For example, in situ formed hydrogels formed from thermosensitive block copolymers have also been proposed as sustained release matrices for drugs. They have the advantage that there is no chemical reaction involved in the gel formation. These copolymer hydrogels are usually designed for macromolecular drugs such as proteins and hormones. The disadvantage of such temperature sensitive hydrogels is the practicality of using such a gel in injection.

More recently, amphiphilic block copolymers have attracted special interest for fundamental research as well as applications because of their unique chain architectures and physical properties in solid state as well as in solutions. Forster, S. et al., *Adv. Mater.* 10:195-217 (1998); Alexandridis, P. *Curr. Opin. Colloid Interface Sci.* 1:490-501 (1996). They have been extensively studied as building blocks in supramolecular polymer chemistry for highly ordered self-assembled structures. Forster (1998), Alexandridis (1996); Vanhest, J. et al., W. *Science* 268:1592-1595 (1995); Jenekhe, S. et al., *Science* 283:372-375 (1999); Kukula, H. et al., *J. Am. Chem. Soc.* 124:1658-1663 (2002). Amphiphilic block copolymers have been considered as biomaterials that take advantage of this self-assembly. The studies have resulted in biomaterials with novel macroscopic properties, which are used for controlled drug delivery and tissue engineering. Jeong, B. et al., *Adv. Drug Delivery Rev.* 54:27-51 (2002); Kissel, T. et al., *Adv. Drug Delivery Rev.* 54:99-134 (2002).

Poly(ethylene oxide) (PEO) is widely used as a hydrophilic and biocompatible polyether. Herold, D. et al., *Biochem. Pharmacol.* 38:73-76 (1989). Amphiphilic ABA triblock copolymers including PEO as the hydrophilic segment have previously been studied and described for use as biomaterials. The term ABA is used herein to refer to a polymer including a center segment of a first polymer, referred to as a B block polymer, and first and second end segments of a second polymer, referred to as an A block polymer. As a typical example, commercially available poly(ethylene oxide)-poly(propylene oxide)-poly(ethylene oxide) (PEO-PPO-PEO, Pluronics™) triblock copolymers have been extensively studied in terms of their phase behavior and potential application for drug delivery. Alexandridis, P. et al., *Colloids Surf.* 96:1-46 (1995); Bromberg, L. et al., *Adv. Drug Del Rev.* 31:197-221 (1998). Recently, more attention has been focused on amphiphilic ABA triblock copolymers of PEO with biodegradable polyesters. Synthesis and characterization of triblock copolymers consisting of PEO and polyesters such as poly(L-lactic acid) (PLLA), poly(glycolic acid) or their copolyesters have been reported. Jeong, B. et al., *Nature* 388:860-862 (1997); Jeong, B. et al., *Macromolecules* 32:7064-7069 (1999); U.S. Pat. No. 5,384,333; U.S. Pat. No. 5,702,717; U.S. Pat. No. 4,716,203; U.S. Pat. No. 5,476,909. Such amphiphilic block copolymers tend to form micelles or even gels in water, which are potentially useful for injectable drug delivery systems.

Another interesting hydrogel system consists of polyrotaxanes created by linear polymers such as poly(ethylene oxide) (PEO) penetrating the inner cavity of cyclodextrins (CDs) to form inclusion complexes with a necklace-like supramolecular structure. Harada A. et al., *Nature* 356:325 (1992); Li J. et al., *Polym. J.* 26:1019 (1994). However, only high molecular weight PEO can form hydrogels with α-CD, and the dissociation of the hydrogel in aqueous solution is rapid because of the hydrophilic nature of PEO.

Injectable drug delivery systems using related hydrogels are disclosed in US Patent Application 2002/0019369 A1, in the name of inventors Li et al., entitled Injectable Drug Delivery Systems with Cyclodextrin-Polymer Based Hydrogels, the disclosure of which is hereby expressly incorporated by reference. This application discloses cyclodextrin polymer-based injectable compositions formed from CD, a polymer that is poly(ethylene glycol) (PEG), a PEG derivative, or a PEG copolymer, and a drug. Reference is made to the use of poly(propylene glycol) or other poly(alkylene glycols) as the polymer in the system. While the polymer hydrogels disclosed in this publication provide promising sustained release systems, they have not been demonstrated to provide optimized release kinetics for sustained release of longer than one week.

Poly[(R)-3-hydroxybutyrate] (PHB) is an optically active biodegradable polyester synthesized as a carbon and energy storage material by many microorganisms. Doi, Y. *Microbial Polyesters*; VCH Publisher, New York (1990).

U.S. Pat. No. 5,702,717 to Cha et al. discloses thermosensitive biodegradable copolymers made up of a hydrophobic A polymer block that may is a poly($\alpha$-hydroxy acid) or a poly(ethylene carbonate), and a hydrophilic B polymer block that is a poly(ethylene glycol). These polymers are disclosed for drug delivery, and are characterized as exhibiting a reverse thermal gelation behavior. A disclosed list of potential examples of poly($\alpha$-hydroxy acid) polymer blocks includes hydroxybutyric acid; however this is a poly($\beta$-hydroxyalkanoate), and does not fall within the polymer class taught by Cha et al., nor would it likely exhibit all of the characteristics sought by Cha et al. Further, Cha et al. utilize a synthesis process that entails ring-opening polymerization of cyclic monomers, which may result in potentially undesirable racemization of the poly($\alpha$-hydroxy acid)s.

SUMMARY OF THE INVENTION

The present invention provides a drug delivery system that includes a hydrogel formed from cyclodextrin and an amphiphilic copolymer that includes an A polymer block comprising a poly(alkylene oxide) and a B polymer block comprising a poly(hydroxyalkanoate), and a therapeutically effective amount of at least one therapeutic agent intimately contained within the hydrogel.

The present invention also provides a process for synthesizing an amphiphilic ABA triblock copolymer, including poly(ethylene oxide) as an A block polymer and poly(3-hydroxybutyrate) as a B block polymer. The process entails: converting poly(3-hydroxybutyrate) into telechelic poly(3-hydroxybutyrate)-diol with a lower molecular weight; producing methoxy-poly(ethylene oxide)-monocarboxylic acid from methoxy-poly(ethylene oxide); and coupling the poly(3-hydroxybutyrate)-diol with the methoxy-poly(ethylene oxide)-monocarboxylic acid using 1-3-dicyclohexylcarbodiimide to yield the ABA triblock copolymer.

The present invention also provides a process for forming a hydrogel drug delivery system, by combining cyclodextrin, a therapeutically effective amount of at least one therapeutic agent in an aqueous base fluid, and an amphiphilic copolymer, wherein the copolymer includes an A polymer block comprising a poly(alkylene oxide) and a B polymer block comprising a poly(hydroxyalkanoate).

In another aspect of the invention, a method of treating a human or other mammal in need thereof with at least one therapeutic agent is provided. The method provides for administering the at least one therapeutic agent in a drug delivery system, the drug delivery system comprising a hydrogel formed from cyclodextrin and an amphiphilic copolymer, wherein the copolymer includes an A polymer block comprising a poly(alkylene oxide) and a B polymer block comprising a poly(hydroxyalkanoate), wherein a therapeutically effective amount of the at least one therapeutic agent is intimately contained within the hydrogel.

In one preferred embodiment of the invention, the A polymer block is poly(ethylene oxide) (PEO) and the B polymer block is poly[(R)-3-hydroxybutyrate] (PHB). The copolymer used to form a hydrogel with $\alpha$-cyclodextrin ($\alpha$-CD) in this embodiment is a triblock PEO-PHB-PEO copolymer.

Amphiphilic triblock copolymers of an embodiment of the present invention, using PEO as end segments and PHB as a mid-segment, have interesting properties because PHB is highly crystalline and hydrophobic. In addition, PHB has a lower in vivo degradation rate than PLLA and many other conventionally used biopolyesters. Gogolewski, S. et al., *J. Biomed. Mat. Res.* 27:1135-1148 (1993). Therefore, the PEO-PHB-PEO triblock copolymers may be more promising for long-term implantation or controlled delivery of drugs than previously developed polymers.

In addition to the self-assembly of the complexes between $\alpha$-CD and PEO blocks, the hydrophobic-hydrophobic interaction between the PHB mid-segment blocks further strengthens the hydrogel network. The properties of the hydrogels can be fine-tuned by adjusting the molecular weights and the molar ratio of PHB and PEO, rendering them potentially attractive for a variety of biomedical applications such as for delivery of proteins, peptides, genes, small molecules, antibodies and fragments thereof and human recombinant proteins, antigens, DNA, RNA or DNA nanoparticles, and for tissue engineering.

The PEO-PHB-PEO hydrogels of the invention have greatly increased sustained release characteristics relative to other known hydrogels, due in part to the increased hydrophobicity of the midsection, to a surprising extent. These hydrogels also exhibit enhanced stability, form gels more rapidly, and require the use of less cyclodextrin, minimizing any undesirable side effects, such as potential inflammation, that may occur if excessive cyclodextrin is utilized.

The PEO-PHB-PEO triblock copolymers of the present invention have a strong tendency toward micelle formation in aqueous medium. Micelle formation from the copolymers of the present invention is relatively temperature-insensitive. This temperature insensitivity is unexpected when compared to the relative temperature instability of micelles formed from other poly($\alpha$-hydroxyalkanoic acids) such as PLLA or PGA (Jeong (2002); Kissel (2002); Jeong (1997); Jeong (1999)), given that PHB and PLLA have similar chemical structures. The micelles of the present invention are thus well suited for drug delivery, such as over a range of 15 to 45 degrees C., because they do not tend to break down prematurely at higher temperatures within this range, and do not readily aggregate to larger sizes at lower temperatures within this range.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
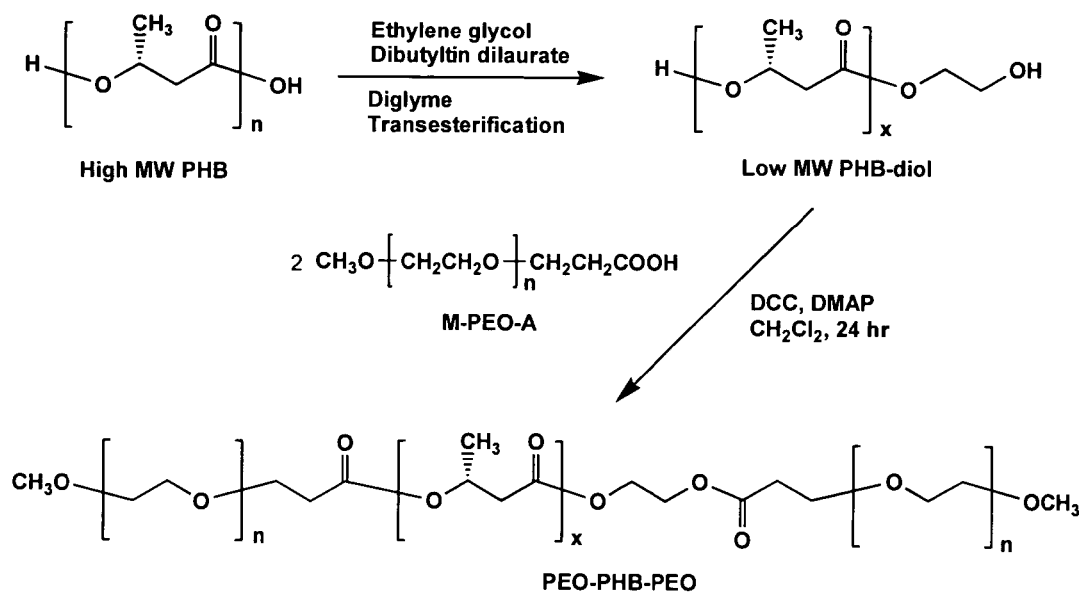
FIG. 1 provides a chemical reaction scheme for the synthesis of poly(ethylene oxide)-poly[(R)-3-hydroxybutyrate]-poly(ethylene oxide) (PEO-PHB-PEO) copolymer in accordance with an embodiment of the invention.

The present invention provides a drug delivery system that includes a hydrogel formed from cyclodextrin and an amphiphilic copolymer that includes an A polymer block comprising a poly(alkylene oxide) and a B polymer block comprising a poly(hydroxyalkanoate), and a therapeutically effective amount of at least one therapeutic agent intimately contained within the hydrogel. In one preferred embodiment of the invention, the A polymer block is poly(ethylene oxide) (PEO) and the B polymer block is poly[(R)-3-hydroxybutyrate] (PHB), and the copolymer is the triblock ABA copolymer PEO-PHB-PEO. The A and B block polymer components of the poly(alkylene oxide)-poly(hydroxyalkanoate)-poly(alkylene oxide) copolymers of the present invention will now be described.

Poly(alkylene oxide)s

A hydrophilic poly(alkylene oxide) end segment structure (the A block polymer) is used in the triblock copolymers of the present invention. The poly(alkylene oxide) is suitably selected from poly(ethylene oxide), poly(tetramethylene oxide) and poly(tetrahydrofuran). A preferred poly(alkylene oxide) for use in the present invention is poly(ethylene oxide) (PEO) or a derivative thereof, and most preferably is PEO. PEO is also referred to as poly(ethylene glycol), and as used herein the term poly(ethylene oxide) (and the abbreviation PEO) is intended to also refer to poly(ethylene glycol) (PEG).

The poly(alkylene oxide) may have different forms and different end groups. For example, in the case of PEO, the PEO derivatives may have different structures, e.g. star-shaped PEO, comb-like PEO, etc. The poly(ethylene oxide) may be in the form of modified molecules, e.g. PEGylated polysaccharides, PEGylated poly(amino acid)s, PEGylated proteins, etc. In addition, a polyamine derivative of PEO, e.g. PEGylated poly(ethylene imine) or PEGylated polylysine, may be used.

The relative molecular mass (Mr) range of PEO or other poly(alkylene oxide) utilized as the A block polymer in the copolymers of the present invention is suitably 500 to 20,000, and preferably is 2,000 to 10,000.

Poly(hydroxyalkanoate)s

A highly hydrophobic poly(hydroxyalkanoate) midsection structure (B block polymer) is used in the triblock copolymers of the present invention. Suitable poly(hydroxyalkanoate)s are: a) relatively hydrophobic so the hydrophobic-hydrophobic interaction between the polymer chains facilitates the macromolecular assembly and reduces the concentration of CD needed; b) biodegradable; and c) nontoxic and biocompatible.

Suitable hydrophobic B polymer blocks for use in the present invention are poly(hydroxyalkanoate)s. Examples of suitable poly(hydroxyalkanoate)s for use in the present invention include: poly[(R)-3-hydroxybutyrate] (PHB), also referred to as poly[(R)-3-hydroxybutryic acid] or poly(β-hydroxy acid); poly[(R)-4-hydroxybutyrate] (PGHB); poly [(R)-3-hydroxyvalerate] (PHV); poly[(R)-3-hydroxybutyrate]-co-poly[(R)-3-hydroxyvalerate] (PHB/HV); poly [(R)-3-hydroxyhexanoate] (PHHx); poly[(R)-3-hydroxyheptanoate] (PHHp); (S) enantiomers of each of the above (R) enantiomers; racemic mixtures of the above (S) and (R) enantiomers; and mixtures of the above poly(hydroxyalkanoate)s. Preferred poly(hydroxyalkanoate)s are poly (β-hydroxy alkanoate)s, and more specifically are poly [(R)-3-hydroxybutyrate] (PHB) and related poly[(R)-3-hydroxyalkanoate]s. A most preferred poly(hydroxyalkanoate) for use in the present invention is PHB.

The relative molecular mass (Mr) range of PHB or other poly(hydroxyalkanoate) utilized as the B block polymer in the copolymers of the present invention is suitably 500 to 20,000, preferably is 2,000 to 10,000, more preferably 2,500 to 7,500 and most preferably is 3,000 to 5,000.

The Copolymer

The present invention provides amphiphilic copolymers of poly(alkylene oxide) and poly(hydroxyalkanoate) produced with a unique synthesis process, described further herein below. Preferably these copolymers are ABA triblock copolymers, such as PEO-PHB-PEO by way of example. Such triblock copolymers of the invention form hydrogels with cyclodextrin, and are useful for sustained release drug delivery and other biomedical applications. The present invention is also directed to AB block copolymers of a poly(alkylene oxide) and a poly(hydroxyalkanoate), such as PEO-PHB by way of example. It is believed that such AB block copolymers will also form useful hydrogels with cyclodextrin. Thus, while triblock ABA polymers are preferred, all embodiments of the invention described herein should be understood to also apply to AB block copolymers of a poly(alkylene oxide) and a poly(hydroxyalkanoate). Other variations of the polymers of the present invention are also possible. For example, a bulky blocking group may be conjugated to the end of the polymer chain via a biodegradable linkage, e.g. L-phenylalanine, L-tryptophan, nicotinyl groups, etc.

The molecular weight of the PEO-PHB-PEO polymers of the present invention is suitably between 1,000 and 50,000, and preferably is between 5,000 and 35,000.

The copolymers of the present invention can be formulated to be bioabsorbable, biodegradable, biocompatible, and are capable of forming hydrogel with cyclodextrin. Bioabsorbable means the polymer is capable of disappearing from its initial application site in the body, with or without degradation of the dispersed polymer molecules. Biodegradable means that the polymer is capable of breaking down or degrading within the body, by hydrolysis or enzymatic degradation. Biocompatible means that all of the components are nontoxic in the body.

Cyclodextrins

Cyclodextrin (i.e., a cylcodextrin) is used in the present invention as a complexing agent, to complex segments of the triblock copolymer. The clustering of these cyclodextrin-threaded polymers then form a hydrogel. Cyclodextrins are a series of natural cyclic oligosaccharides composed of six, seven, eight, or more D (+) glycopyranose units linked by alpha 1, 4 linkages. Cyclodextrins are biodegradable and biocompatible and may be naturally or artificially synthesized. Cyclodextrin may be synthesized naturally by microorganisms, for example. Cyclodextrin may be artificially modified to manipulate its properties, such as improving solubility, complex-forming capability, and specificity. Cyclodextrin as used herein refers to all forms of the natural and artificially modified forms. Suitable cyclodextrins include α-cyclodextrin, β-cyclodextrin, γ-cyclodextrin and derivatives thereof, including hydrophobic derivatives, hydrophilic derivatives, charged cyclodextrins, and the like. A preferred cyclodextrin is α-cyclodextrin.

Polymer Synthesis

The procedures for synthesis of the PEO-PHB-PEO triblock copolymers are presented in the reaction scheme of FIG. 1. To synthesize PEO-PHB-PEO triblock copolymer in accordance with the present invention, the polymer precursors are first prepared using conventional techniques. Natural source PHB has a high molecular weight, and has one hydroxy-terminal group and one carboxy-terminal group. Natural source PHB is also pure in optical activity. High molecular weight natural source PHB is converted into telechelic hydroxyl-terminated PHB (PHB-diol) with lower molecular weight by a transesterification reaction with ethylene glycol, using known techniques. For example, the transesterification reaction may be carried out in diglyme (diethylene glycol dimethyl ether) with dibutyltin dilaurate as a catalyst. The transesterification reaction is allowed to proceed for a few hours to overnight, to produce PHB-diol with average molecular weight ranging from a few hundred to a few thousand, as determined by gel permeation chromatography (GPC). Methoxy-PEO-monocarboxylic acid (M-PEO-A) prepolymers are suitably prepared by reaction of Methoxy-PEO with succinic anhydride in the presence of 4-(dimethylamino)pyridine (DMAP) and triethylamine in 1,4-dioxane, using known techniques.

These polymer precursors, i.e., prepolymers, are then coupled, in accordance with a method of the present invention, to yield the desired triblock copolymer. The prepolymers (PHB-diols and M-PEO-A) are preferably first dried, because the coupling reaction is humidity sensitive. The bifunctionalized PHB-diols are coupled with M-PEO-A using 1,3-dicyclohexylcarbodiimide (DCC) as a coupling agent to yield the PEO-PHB-PEO triblock copolymers. Again, because of humidity sensitivity, the coupling reaction is carried out in dried methylene chloride under a nitrogen atmosphere. The M-PEO-A should be in excess in the coupling reaction to ensure that all PHB-diol is converted to the triblock copolymer.

The target triblock copolymer is then isolated and purified from the reaction mixture through one or more precipitations and careful fractionations with mixed solvents, suitably methanol/diethyl ether or chloroform/diethyl ether. The PHB blocks of the polymer retain a well-defined (R) racemic configuration.

In addition to the production of the triblock copolymer using the (R) enantiomer of PHB, this synthesis process is also expected to be useful for the production of (S) enantiomers of PHB and racemic mixtures of (S) and (R) enantiomers and other related poly(3-hydroxyalkanoate)s and their copolymers.

Hydrogel Assembly

Supramolecular self-assembly between the amphiphilic triblock copolymers of the present invention and cyclodextrin forms an injectable hydrogel that is physically cross-linked. Supramolecular self-assembly concerns the spontaneous association of multiple molecular components into a specific phase having well-defined microscopic organization and macroscopic characteristics. In the hydrogels of the present invention, the PEO (for example) segments self-assemble with each other, while hydrophobic interactions occur between the PHB (for example) mid-segments. Drugs can be delivered in a sustained manner from an in vivo matrix or carrier formed from a cyclodextrin-polymer based injectable hydrogel of the present invention.

The cyclodextrin-polymer based injectable hydrogel composition may be prepared in any suitable manner. For formation of a hydrogel without a drug, cyclodextrin is combined with an aqueous carrier fluid (e.g., deionized water or saline). The cyclodextrin solution is mixed and then the amphiphilic copolymer component (e.g., PEO-PHB-PEO) is added. The mixture is cooled, generally to a temperature of 0° C. to 25° C., and preferably to a refrigerated temperature such as 4° C. The resulting product is a white viscous hydrogel.

If the hydrogel is being prepared for use in the delivery of a drug, the drug in an aqueous solution is suitably initially combined with the cyclodextrin, followed by addition of the copolymer. Alternately, the drug solution may first be combined with the copolymer. The aqueous solution in which the drug is initially contained is a pharmaceutically acceptable injectable aqueous fluid. The pharmaceutically acceptable injectable aqueous fluid may be, but is not limited to, injectable saline. If desired, the aqueous fluid may also contain buffering agents and/or preservatives. Suitable buffering agents include, but are not limited to, alkali or alkali earth carbonates, phosphates, bicarbonates, citrates, borates, acetates, and succinates. Suitable preservatives include, but are not limited to, sodium bisulfite, sodium thiosulfate, ascorbate, benzalkonium chloride, chlorobutanol, thimersol, phenylmercuric borate, parabens, benzyl alcohol and phenylethanol. Preservatives and buffering agents, if used, will be selected based in part on compatibility with the therapeutic agents utilized.

Preferably the polymer is in an aqueous solution, which forms a hydrogel with cyclodextrin. For example, suitable aqueous polymer solutions contain about 1% to about 80% polymer, preferably about 10% to about 40%. Suitable hydrogels contain about 1.0% to 20% cyclodextrin (w/w) (based on the weight of total solution), preferably about 5% to 15% cyclodextrin. As noted, the hydrogel is typically formed using an aqueous carrier fluid. For example, typical aqueous solutions contain about 1% to about 80% polymer, preferably about 10% to about 40%.

The cyclodextrin and polymer are combined in sufficient amounts and relative proportions, in accordance with the invention, to provide an injectable hydrogel having desired release kinetics (for drug delivery applications) and physical properties (i.e., sol viscosity and gel-sol transition characteristics), for a particular application. When used for injectable drug delivery systems, a quantity of cyclodextrin is used sufficient to yield a gel that is injectable as a sol (due to shear induced transition) through a hypodermic needle. Suitably, the weight ratio of cyclodextrin to polymer is from 0.05:1.0 to 0.5:1.0 (i.e., the cyclodextrin is included at 5%-80% of the weight of the polymer). Preferably, the cyclodextrin is included at 5% to 50% of the weight of the polymer.

It is desirable to use the minimum quantity of cyclodextrin necessary to achieve desired release kinetics (for drug delivery) and physical characteristics, to avoid levels of cyclodextrin that could lead to an inflammatory response in vivo. The hydrogels of the present invention are believed to require substantially less cyclodextrin to form a gel, such as 50% less, than conventional hydrogels formed by cyclodextrin and homopolymeric PEOs. As one extreme example, some copolymers with certain PEO/PHB combinations can form gels without CD. However, with the CD, the gels give significantly improved release kinetics. This is important because the quantity of CD can be selected to adjust the release kinetics of the gels.

Hydrogel Properties and Additional Components

The hydrogel of the present invention is bioabsorbable and biodegradable, and is biocompatible. It is believed to be thermosensitive, is thixotropic, and undergoes reversion between gel and sol under certain conditions. The gel-sol transition temperature is generally above room temperature, which depends on the composition of the gel, as well as on the chemical structure and molecular weight of the copolymer. The formation of hydrogels from triblock ABA polymers of the present invention, including PEO as the A block and PHB as the B block, has been found to be relatively temperature insensitive. At temperatures ranging from 10 to 45 degrees C., the formation of gels and micelles is primarily dependent on concentration rather than temperature. Hydrogels and micelles formed with this polymer, which is difficult to dissociate at low temperature and difficult to aggregate to larger size at high temperature, are thus stable and readily handled for drug delivery.

Due to its thixotropic nature, the hydrogel will transform to a sol when subjected to sufficient shear force, rendering the hydrogel (and any drugs contained therein) injectable. For example, the hydrogel can be made to pass through needles as small as 27 G.

The pH of the hydrogel is generally about 6.5 to about 7.8, which is a suitable pH level range for injection into the body. The pH level may be adjusted by use of any suitable acid or base, such as hydrochloric acid or sodium hydroxide.

The hydrogel composition may also contain a secondary polymer, which may complex with the drug, conjugate the drug, or both. The secondary polymer may suitably be a polyester, polyurethane, polyamide, polyether, polysaccharide, poly(amino acid), polypeptide, or a protein. Preferably the secondary polymer is a di- or mono-functional polymer or polyionic polymer with (polyethylene glycol) segments. In the case where drugs conjugate or complex to the hydrogels, then the hydrogel formulations act not only as a matrix but also a carrier of the drugs. This means that the drug is not only physically entrapped in the hydrogel, but also is complexed or conjugated to the molecules that form the hydrogel. The secondary polymer may also be used to alter the properties, such as porosity and viscosity, of the hydrogel matrix. The amount of the secondary polymer should be sufficient to achieve the desired result, e.g., a sufficient amount to complex with and/or conjugate the drug.

The properties of the hydrogels are tunable by using different polymer block molecular weights, by adjusting the cyclodextrin content, and through the use of secondary polymers. For example, the hydrogel may be adjusted to be a more flexible hydrogel or a more rigid hydrogel. The hydrogel structure can be tailored to have variable viscosity and longer or shorter drug release rates, as discussed further below. The degree of hydrophobicity of the poly(hydroxyalkanoate) can also be selected for a desired sustained release rate.

The hydrogel may also carry DNA nanospheres. DNA nanospheres are nanoparticles synthesized by salt-induced complex coacervation of DNA and polycations such as gelatin and chitosan as gene delivery vehicles. Leong, K. et al., *Journal of Controlled Release* 53:183-193 (1998). PEG copolymers with DNA condensing or binding segments may form hydrogels with cyclodextrin, while the polymers condense or bind DNA and form DNA nanospheres in the hydrogels.

Therapeutic Agents and Methods for Sustained Drug Release

The hydrogel of the present invention is suitable for use as a sustained, controlled release matrix for drugs. When this hydrogel matrix is coupled with one or more therapeutic agents contained intimately therein, a biodegradable sustained release drug delivery system is provided. The terms "sustained release" (i.e., extended release or controlled release) are used herein to refer to a drug delivery system or composition that is introduced into the body of a human or other mammal, or that is applied to an open wound, burn or tissue surface or into a body cavity or potential body space, and that continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the composition, or a matrix or component thereof, or as the result of metabolic transformation or dissolution of the therapeutic agent(s) or conjugates of therapeutic agent(s).

The duration of extended release is dependent on the molecular weights of the block polymers, particularly the molecular weight of the hydrophobic poly(hydroxyalkanoate) section (e.g., PHB). The release rate may be altered in accordance with the invention to achieve a desired duration of therapeutic response by selecting: a particular poly(hydroxyalkanoate); the stereo-isomeric state of the selected poly(hydroxyalkanoate); the molecular weight of the selected poly(hydroxyalkanoate); and the relative quantity of cyclodextrin used in the hydrogel, to achieve a desired duration and rate of sustained release. The molecular weight and selection of the hydrophilic poly(alkylene oxide) also impacts the sustained release kinetics, but to a lesser extent than the hydrophobic poly(hydroxyalkanoate) component. Secondary polymers may also be utilized to change the release kinetics, as discussed further above. Hydrogels of the present invention can provide sustained release over a period of one or more days, and suitably provide an extended release of greater than 5 days, more preferably greater than one week, still more preferable two weeks or longer, and potentially one month or longer by adjustment of the molecular weights of the block polymers and the copolymer, as well as the cyclodextrin content within the hydrogel of the present invention and the potential use of secondary polymers.

A variety of therapeutic agents, i.e. drugs, may be delivered in the hydrogels of the present invention. As used herein, the terms "therapeutic agents" and "drugs" are intended to encompass biologically active molecules, including peptides, proteins (e.g., cytokines, growth factors, angiogenesis factors, soluble receptors, antibodies and fragments thereof and human recombinant proteins), small molecules, genes, antigens (e.g., vaccines), DNA, RNA and DNA nanoparticles. The terms "drug" and "therapeutic agent" as used herein are also intended to encompass not only compounds or species that are inherently pharmaceutically or biological active, but also materials which include one or more of these active compounds or species, as well as conjugations, modifications, and pharmacologically active fragments, and antibody derivatives thereof.

The present invention also provides a method of manufacturing a medicament formed from the amphiphilic triblock copolymers described herein with cyclodextrin and one or more therapeutic agents. The invention thus provides supramolecular hydrogels based on an inclusion complexation between cyclodextrin and the triblock copolymer, in which one or more therapeutic agents may be intimately contained. These hydrogels are promising for controlled delivery of proteins or peptide drugs.

For drug delivery systems, the therapeutic agents are suitably compounded in a pharmaceutically acceptable injectable aqueous base, and the therapeutic agent(s) may be any drug suitable for injection or other mode of delivery, or combinations of such drugs. Suitable drugs include, but are not limited to, analgesics, anesthetics, anti-arthritic drugs, disease modifying anti-rheumatic drugs (DMARDS), anti-asthma drugs, anticoagulants, anticonvulsants, antidepressants, antidiabetics, antineoplastics, antipsychotics, antihypertensives, antibiotics, antihistamines, decongestants, anti-inflammatories, muscle relaxants, anti-parasitic drugs, antiviral drugs, anti-restenotic agents, anti-spasm agents, chondroprotective agents, anti-adhesion agents, anti-tumor cell invasion agents, vasorelaxants, vasoconstrictors, immunosupressants and other biologically active molecules, including peptides, proteins (e.g., cytokines, growth factors, angiogenesis factors, soluble receptors, antibodies and fragments thereof and human recombinant proteins), small molecules, genes, antigens (e.g., vaccines), DNA, RNA and DNA nanoparticles.

The drug may suitably be in a macromolecular form (i.e., a drug that is normally a macromolecule or a drug that is a smaller molecule that has been conjugated, PEGylated or otherwise converted to a macromolecule) or in a low molecular weight form. Macromolecular forms are very well suited for delivery in the present hydrogels. Thus macromolecules such as proteins, which include growth factors, cytokines, antibodies, enzymes, etc., may be delivered in the hydrogels of the invention. For effective and uniform sustained release, low molecular weight drugs may suitably be conjugated, such as to poly(ethylene glycol) by way of example, to form a macromolecule that is then incorporated into the hydrogel. Drugs that are small molecules may suitably be contained within or linked to microparticles and/or nanoparticles, e.g., DNA nanospheres, for incorporation into the hydrogels of the invention. Because the hydrophobic midsection segments of the triblock copolymers of the present invention can form micelles, the hydrogels can also trap hydrophobic drugs, e.g., paclitaxel (Taxol™), including hydrophobic small molecules.

Additional examples of therapeutic agents that may suitably be delivered in the hydrogels of the present invention are disclosed in U.S. Pat. No. 6,420,432 issued to Demopulos et al., entitled Surgical Irrigation Solution and Method for Inhibition of Pain and Inflammation, and International PCT Patent Application WO 01/07067 in the name of Demopulos et al., entitled Solutions and Methods for Inhibition of Pain, Inflammation and Cartilage Degradation, the disclosures of which are hereby expressly incorporated by reference. U.S. Pat. No. 6,420,432 discloses analgesic, anti-inflammatory, anti-spasm, and anti-restenotic agents that are delivered alone or in combination to inhibit pain, inflammation, smooth muscle spasm or restenosis. The selection of agents is determined for given applications to inhibit undesirable mechanisms arising from any trauma, condition or other reason, including surgical, operative, interventional or diagnostic procedures, such as delivery of anti-inflammatory/anti-pain agents intra-articularly during arthroscopic procedures, delivery of anti-inflammatory/anti-pain and/or anti-spasm agents to the urogenital tract during urogenital procedures, delivery of anti-pain/anti-inflammation, anti-spasm and/or anti-restenosis agents intravascularly during cardiovascular procedures, or delivery of anti-pain/anti-inflammatory agents to a wound during general surgical, ophthalmologic, periodontal or other general surgical procedures. Disclosed anti-inflammation/analgesic agents include: serotonin receptor antagonists; serotonin receptor agonists; histamine receptor antagonists; bradykinin receptor antagonists; kallikrein inhibitors; tachykinin receptor antagonists, including neurokinin, and neurokinin$_2$ receptor subtype antagonists; calcitonin gene-related peptide (CGRP) receptor antagonists; interleukin receptor antagonists; inhibitors of enzymes active in the synthetic pathway for arachidonic acid metabolites, including (a) phospholipase inhibitors, including $PLA_2$ isoform inhibitors and $PLC_\gamma$ isoform inhibitors, (b) cyclooxygenase inhibitors, and (c) lipooxygenase inhibitors; prostanoid receptor antagonists including eicosanoid EP-1 and EP-4 receptor subtype antagonists and thromboxane receptor subtype antagonists; leukotriene receptor antagonists including leukotriene $B_4$ receptor subtype antagonists and leukotriene $D_4$ receptor subtype antagonists; opioid receptor agonists, including μ-opioid, δ-opioid, and κ-opioid receptor subtype agonists; purinoceptor agonists and antagonists including $P_{2X}$ receptor antagonists and $P_{2Y}$ receptor agonists; and adenosine triphosphate (ATP)-sensitive potassium channel openers. Disclosed anti-spasm agents include: serotonin receptor antagonists; tachykinin receptor antagonists; ATP-sensitive potassium channel openers; calcium channel antagonists; endothelin receptor antagonists; calcium channel antagonists; and nitric oxide donors (enzyme activators). Disclosed anti-restenosis agents include: antiplatelet agents including: (a) thrombin inhibitors and receptor antagonists, (b) adenosine disphosphate (ADP) receptor antagonists (also known as purinoceptor$_1$ receptor antagonists), (c) thromboxane inhibitors and receptor antagonists and (d) platelet membrane glycoprotein receptor antagonists; inhibitors of cell adhesion molecules, including (a) selectin inhibitors and (b) integrin inhibitors; anti-chemotactic agents; interleukin receptor antagonists; and intracellular signaling inhibitors including: (a) protein kinase C (PKC) inhibitors and protein tyrosine phosphatases, (b) modulators of intracellular protein tyrosine kinase inhibitors, (c) inhibitors of src homology$_2$ (SH2) domains, and (d) calcium channel antagonists. When such compositions are delivered during urologic, general surgery or oncological procedures, anti-adhesion or anti-tumor invasion/adhesion/metastasis agents may also be included, alone or in combination, such as: CD44 receptor antagonists; integrin receptor antagonists and selectin receptor antagonists; proteinase inhibitors; protein tyrosine kinase inhibitors; protein kinase C inhibitors; and mitogen-activated protein kinases (MAPK) inhibitors. Each of these various compositions and procedures may be carried out by delivering the therapeutic agents in the hydrogels of the present invention, to provide an extended release and duration of action.

WO 01/07067 discloses chondroprotective agents that inhibit cartilage catabolism or that promote cartilage anabolism. Disclosed anabolic promoting chondroprotective agents include: interleukin (IL) agonists; members of the transforming growth factor (TGF)-β superfamily, including TGF-β agonists and bone morphogenic protein agonists; insulin-like growth factors; and fibroblast growth factors. Disclosed catabolic inhibitory chondroprotective agents include: IL-1 receptor antagonists; tumor necrosis factor (TNF)-α receptor antagonists; cyclooxygenase-2 specific inhibitors; MAP kinase inhibitors; nitric oxide synthase inhibitors; and nuclear factor kB inhibitors; inhibitors of matrix metalloproteinases; cell adhesion molecules, including integrin agonists and integrin antagonists; anti-chemotactic agents; intracellular signaling inhibitors, including protein kinase C inhibitors and protein tyrosine kinase inhibitors; modulators of intracellular protein tyrosine phosphatases; and inhibitors of SH2 domains. Such chondroprotective compositions may be delivered in the hydrogels of the present invention, such as by intraarticular injection, to provide extended release and duration of action.

The hydrogel and therapeutic agent drug delivery systems of the present invention are suitably injected or otherwise delivered (e.g., by implanting, placing into a body cavity or potential space, coating a tissue surface of the body or coating the surface of an implantable device) to humans or other mammals suffering from a disease state or condition against which the drug(s) included in the drug delivery system are therapeutically effective. By way of non-limiting example, the drug delivery system including appropriate therapeutic agent(s) may be delivered to treat humans or other mammals suffering from traumatic or chronic pain, arthritis, multiple sclerosis and other auto-immune disorders, inflammation and/or pain from trauma or surgery or other operative procedures, anxiety and/or other neurological or psychological disorders, cardiovascular disease or conditions such as hypertension, urologic or gynecologic disorders, cancers subject to treatment with chemotherapeutics, congestion, hormonal disorders or imbalances, etc. The particular drug or drugs used in the hydrogel are the type that a human or other mammal would require for pharmacological treatment of the condition from which the human or other mammal is suffering.

The injectable composition may be injected or implanted into the body of a human or other mammal in any suitable manner, and preferably by injection through a hypodermic needle. For example, the hydrogel may be administered by injection or other means intraarticularly, intravascularly, into the urogenital tract, subcutaneously, intramuscularly, intradermally, intracranially, intrapericardially, intrapleurally, or into any body cavity or potential space. Alternately, the hydrogel may be introduced via a catheter or a syringe to a joint such as during an arthroscopic procedure, or into the urogenital tract, into the vasculature, into the pericardial or pleural space, or into any body cavity or potential space within the body, during operative, surgical, diagnostic or interventional procedures. The hydrogel can be administrated to a confined area or tissue to achieve a higher local concentration of the drug, forming a sustained release depot. In other applications, topical application of the hydrogel to an open surgical or traumatic wound, to a burn, or to the skin or other tissue surface may be carried out.

Additional Biomaterial Applications

The triblock copolymer of the present invention will form micelles, which will remain in a liquid suspension or aggregate to form a gel, depending on concentration. Micelles formed by the biodegradable triblock copolymers produced by the synthesis method described herein above may be used themselves for encapsulation of drugs for controlled release, particularly hydrophobic drugs. The triblock copolymer micelles may also be dried to form microspheres or nanospheres for use in encapsulating drugs as a sustained release formulation. It is believed that techniques suitable for microparticle or nanoparticle formation using the triblock copolymer of the present invention may be adapted from known techniques used for other polymers. Non-limiting examples of such techniques are disclosed in: Song, C., et al., *Journal of Controlled Release* 43:197-212 (1997); Kim, S. et al., *Journal of Controlled Release* 56:197-208 (1998); Kim, I. Et al., *International Journal of Pharmaceutics* 205:165-172 (2000); and Jeong, Y. et al., *International Journal of Pharmaceutics* 188:49-58 (1999), the disclosure of each of which is hereby incorporated by reference. Micelles of the biodegradable triblock copolymers (or microparticles or nanoparticles formed therefrom) can thus be used for systemic delivery, including by way of non-limiting example administration by intravascular, inhalation, oral, intramuscular and subcutaneous routes of administration. Hydrogels of the present invention formed by the biodegradable triblock copolymers and cyclodextrin may also be used as a media for cell culturing and encapsulation, for tissue engineering applications. Synthetic tissue, formed in the hydrogel ex vivo or in vivo, may be implanted within a human or other mammal (such as in synthetic cartilage), or may be applied externally (such as in synthetic skin). Therapeutic agents may be encompassed within the synthetic tissue formed using the triblock copolymer or hydrogel of the present invention, to aid tissue growth, viability or healing.

Hydrogels of the present invention may also have utility as coatings for preventing adhesion formation during surgical procedures. One or more therapeutic agents may also be encompassed in such compositions.

Hydrogels of the present invention, including one or more therapeutic agents, may also be used to coat implantable devices, e.g., stents, catheters, airway tubes, conduits, screws, plates, shunts, artificial joints, artificial hearts or valves, other prostheses, etc. Such devices may be constructed of bioabsorbable or non-bioabsorbable materials. Other biomaterial and biologic applications for the hydrogels described herein are also considered to be within the scope of the present invention.

EXAMPLES

The present invention will be better understood in view of the following examples, which illustrate the synthesis of triblock polymers and hydrogels of the invention, and their properties. The examples are illustrative only, and are not reflective of the invention as a whole.

Example 1

Synthesis and Characterization of Triblock Copolymers a. Synthesis of Triblock Copolymers

Telechelic hydroxylated PHB (PHB-diol) prepolymers with various molecular weights were prepared by a transesterification procedure from the natural PHB and diethylene glycol, with dibutyltin dilaurate as a catalyst in diglyme as reported previously. Thomas, D. et al., *Macromol. Chem. Phys.* 197:1609-1614 (1996). The transesterification reaction was allowed to proceed for a few hours to overnight, to produce PHB-diol with average molecular weights ranging from a few hundred to a few thousand as determined by GPC. M-PEO-monocarboxylic acid (M-PEO-A) prepolymers with Mn of 1820 and 4740 were prepared by reaction of M-PEO with succinic anhydride in the presence of 4-(dimethylamino)pyridine (DMAP) and triethylamine in 1,4-dioxane as reported previously. Bae, Y. et al., *J. Controlled Release* 64:3-13 (2000).

Then, as one example of the invention, these bifunctionalized PHB-diol prepolymers were coupled with M-PEO-A prepolymers (Mn~1820 and 4740) using 1,3-dicyclohexyl-carbodiimide to give the PEO-PHB-PEO triblock copolymers. Because the reaction is humidity sensitive, it was carried out in dried methylene chloride under a nitrogen atmosphere. The targeted triblock polymer was isolated and purified from the reaction mixture through precipitation and careful fractionation from mixed solvents of chloroform/diethyl ether or methanol/diethyl ether.

b. Molecular Characterization of the Triblock Copolymers

Figure 2:
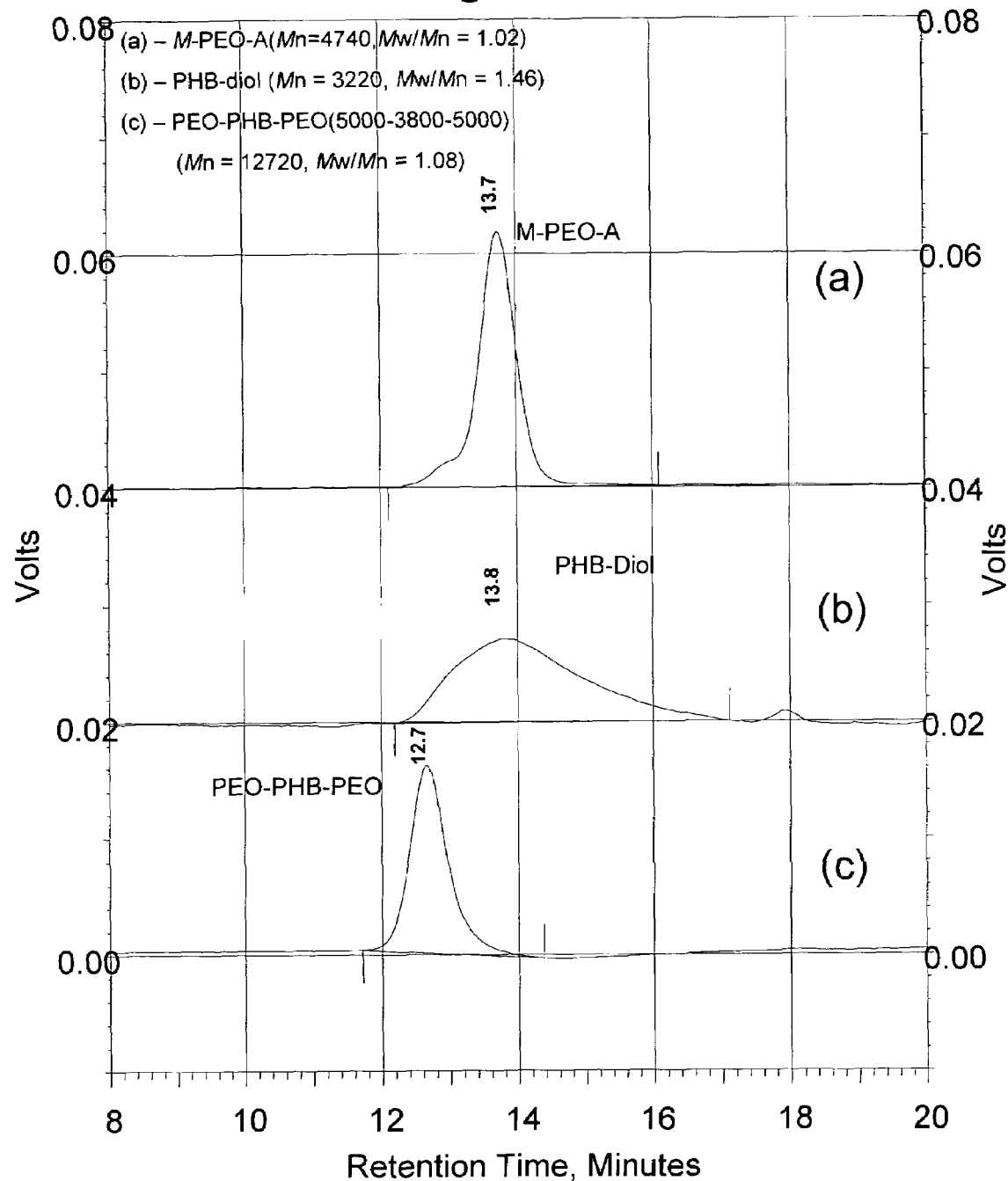
FIG. 2 provides a gel permeation chromatography (GPC) chromatogram for the PEO-PHB-PEO copolymer produced in Example 1 and for the corresponding prepolymers.

Gel permeation chromatography (GPC) analysis was performed to determine the molecular weights and molecular weight distributions of the triblock copolymers. GPC chromatographs of all purified triblock copolymers showed peaks that were unimodal. FIG. 2 shows a typical GPC chromatogram for the PEO-PHB-PEO triblock copolymers together with the corresponding prepolymers. The molecular weight of the PEO-PHB-PEO triblock copolymer is higher than its PEO and PHB precursors, corresponding to the ABA triblock structure.

Figure 3:
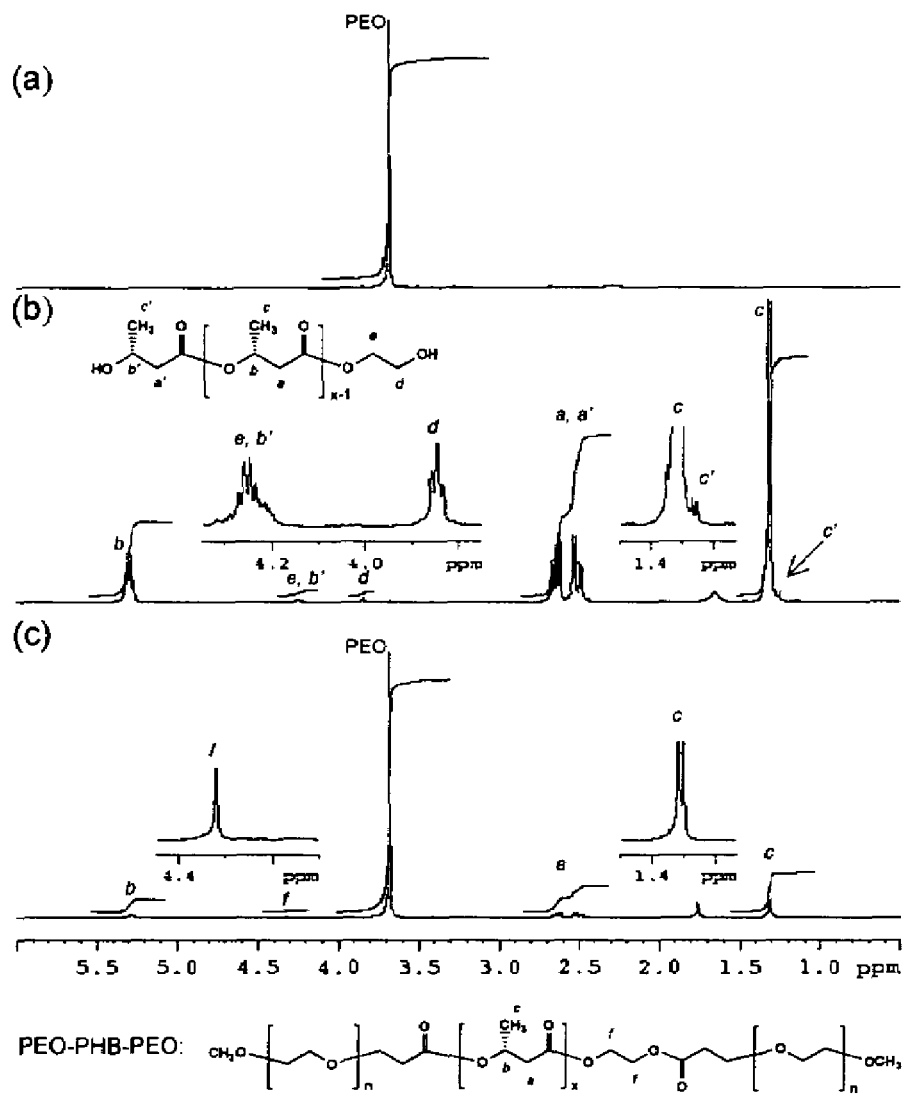
FIG. 3 provides a $^1$H NMR spectra for the PEO-PHB-PEO copolymer produced in Example 1 and for the corresponding prepolymers.

All the triblock copolymers were analyzed by $^1$H NMR spectroscopy, which confirmed that the triblock copolymers contained both PEO and PHB blocks, and gave the lengths of the middle PHB block of the copolymers. FIG. 3 shows the $^1$H NMR spectra of a PEO-PHB-PEO triblock copolymer and its precursor prepolymers. Because the two M-PEG-A prepolymers used in this example were almost monodispersed (molecular weight average/number average (Mw/Mn)=1.03), the molecular weights of PEO blocks in the copolymers can be considered identical to their M-PEO-A prepolymers. Therefore, the molecular weight of the PHB block in the copolymers can be determined from the ratio between integrals of peaks for PHB and PEO segments.

The $^1$H NMR spectra also provide strong evidence for quantitative reaction of the PHB-diol. In FIG. 3b, the protons of the PHB hydroxy end unit clearly appear at 1.26 ppm (doublet) for c' and 4.25 ppm (multiplet) for b' (Li, J. et al., *Bull. Chem. Soc. Jpn.* 70:1887-1893 (1997); Li, J. et al., *Bull. Chem. Soc. Jpn.* 71:1683-1689 (1998)), while the ethylene glycol end group can be seen at 3.84 ppm (triplet) for d and 4.26 ppm (triplet) for e (Thomas, D. et al., *Macromol. Chem. Phys.* 197:1659-1614 (1996)). In FIG. 3c, all peaks for the PHB hydroxy end unit disappear, and those of the ethylene glycol end group become a single peak at 4.32 ppm, confirming the complete conjugation of M-PEO-A to PHB-diol.

Table 1 presents the molecular weights, molecular weight distributions, and compositions (block lengths and PHB contents in weight) of all triblock copolymers synthesized in this example. Two series of triblock copolymers were synthesized using M-PEO-A of Mn 1820 and 4740. Each series of triblock copolymers has middle PHB block lengths ranging from a few hundred to more than 5000. The solid state properties of the triblock copolymers depend on the compositions and ratios between the PHB/PEO block lengths as described later in the following section.

TABLE 1

| Copolymer | $Mn^a$ | $Mw^a$ | $Mw/Mn^a$ | Block length (Mn) | | PHB content (wt %) | |
|---|---|---|---|---|---|---|---|
| | | | | $PEO^a$ | $PHB^b$ | $NMR^b$ | $TGA^c$ |
| PEO-PHB-PEO (2000-0500-2000) | 4500 | 4730 | 1.05 | 1820 | 470 | 11.4 | 12.6 |
| PEO-PHB-PEO (2000-3900-2000) | 7290 | 8000 | 1.10 | 1820 | 3910 | 51.8 | 52.0 |
| PEO-PHB-PEO (2000-5200-2000) | 8120 | 9260 | 1.14 | 1820 | 5230 | 59.0 | 58.3 |
| PEO-PHB-PEO (5000-0800-5000) | 10390 | 11200 | 1.08 | 4740 | 780 | 7.6 | 8.4 |
| PEO-PHB-PEO (5000-3800-5000) | 12720 | 13770 | 1.08 | 4740 | 3820 | 28.7 | 29.7 |
| PEO-PHB-PEO (5000-5500-5000) | 13390 | 16250 | 1.21 | 4740 | 5490 | 36.7 | 38.2 |

[a]Determined by GPC.
[b]Determined by combination of $^1$H NMR and GPC results.
[c]Calculated from TGA results.

Figure 4:
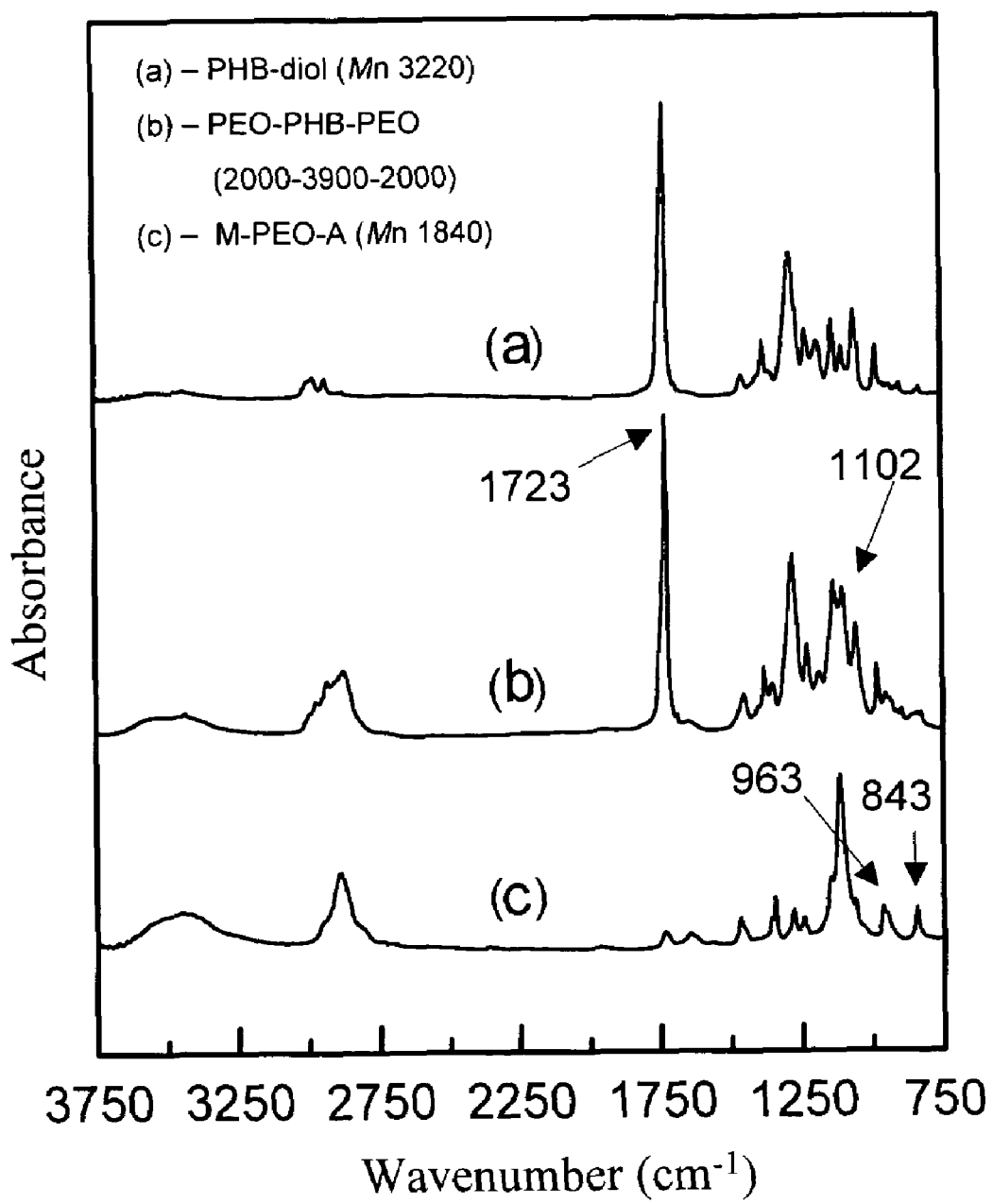
FIG. 4 provides a FTIR spectra for a PEO-PHB-PEO (2000-3900-2000) copolymer produced in accordance with the process of Example 1 and for the corresponding prepolymers.

The FTIR spectra of PEO-PHB-PEO (2000-3900-2000) and its starting PEO and PHB precursors are shown in FIG. 4. All the characteristic absorptions for PHB and PEO precursors appear the spectrum of the triblock copolymer. The carbonyl stretch occurs at 1723 cm$^{-1}$ for the copolymer and PHB precursor. The ether stretch occurs at 1102 cm$^{-1}$ for the copolymer and PEO precursor. The bands at 963 and 843 cm$^{-1}$ are known to be characteristic of the crystalline phase of PEO. Bailey, J. et al., *Poly(Ethylene Oxide)*, Academic Press, New York, (1976). The two peaks appear in the spectrum of the copolymer, and their intensities are associated with the PEO block content and its crystallinity. The result is in good agreement with those from DSC and XRD, which will be used in following sections.

c. Thermal Stability

Figure 5:
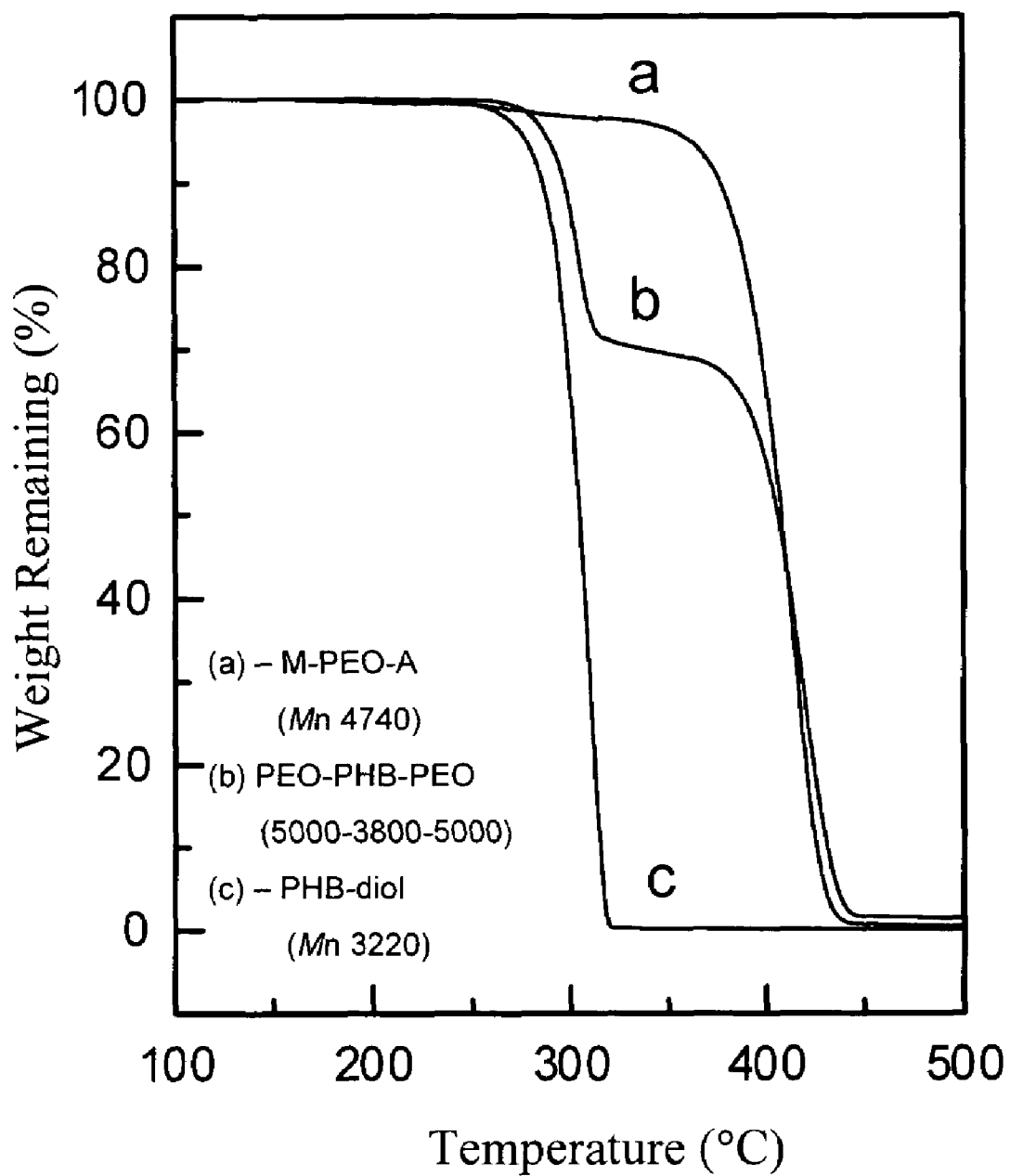
FIG. 5 provides weight loss curves during thermogravimetric analysis (TGA) of a PEO-PHB-PEO copolymer produced in accordance with the process of Example 1 and for the corresponding prepolymers.

The thermal stability of the triblock copolymers was evaluated using thermogravimetric analysis (TGA). FIG. 5 shows the weight loss curves for triblock copolymers and PEO and PHB precursors. The PEO-PHB-PEO triblock copolymers undergo stepwise thermal degradation. The PHB block starts degradation first at about 260° C., then the PEO block starts degradation at about 350° C. It should be noted that the PEO block starts degradation after the PHB block has completed it degradation at 310-320° C. Therefore, the composition of a triblock copolymer and the PHB content can be calculated from this two-step degradation behavior, as listed for various molecular weight copolymers in Table 1. The results are in good accordance with those obtained from $^1$H NMR. The temperatures at which 10% of mass loss has occurred for each block of the copolymers determined from TGA are listed in Table 2. The results show that the triblock copolymers have better thermal stability than their precursors.

TABLE 2

| Polymer | $T_m (° C.)^a$ | | $\Delta H_m (J/g)^b$ | | $X_c^c$ | | $T_d (° C.)^d$ | |
|---|---|---|---|---|---|---|---|---|
| sample | PEG | PHB | PEG | PHB | PEG | PHB | PHB | PEO |
| M-PEO-A (Mn 1820) | 53.2 | | 149.6 | | 73.0 | | | 372.2 |
| M-PEO-A (Mn 4740) | 58.8 | | 165.5 | | 80.7 | | | 379.4 |
| PHB-diol (Mn 3800) | | 155.2 | | 78.2 | | 53.3 | 269.1 | |

TABLE 2-continued

| Polymer | $T_m (° C.)^a$ | | $\Delta H_m (J/g)^b$ | | $X_c^c$ | | $T_d (° C.)^d$ | |
|---|---|---|---|---|---|---|---|---|
| sample | PEG | PHB | PEG | PHB | PEG | PHB | PHB | PEO |
| PEO-PHB-PEO (2000-0500-2000) | 52.0 | | 135.4 | | 66.0 | | 280.6 | 383.3 |
| PEO-PHB-PEO 2000-3900-2000) | 25.4 | 142.3 | 69.1 | 92.2 | 33.7 | 62.8 | 279.8 | 382.9 |
| PEO-PHB-PEO (2000-5200-2000) | 23.3 | 153.6 | 58.3 | 97.8 | 28.4 | 66.7 | 278.2 | 378.0 |
| PEO-PHB-PEO (5000-0800-5000) | 57.7 | | 148.7 | | 72.5 | | 284.8 | 384.7 |
| PEO-PHB-PEO (5000-3800-5000) | 54.1 | 140.2 | 119.4 | 97.8 | 58.2 | 66.7 | 283.8 | 391.0 |
| PEO-PHB-PEO (5000-5500-5000) | 50.4 | 153.2 | 111.0 | 107.8 | 54.1 | 73.6 | 286.0 | 387.8 | d. Solid-State Behavior

Figure 6:
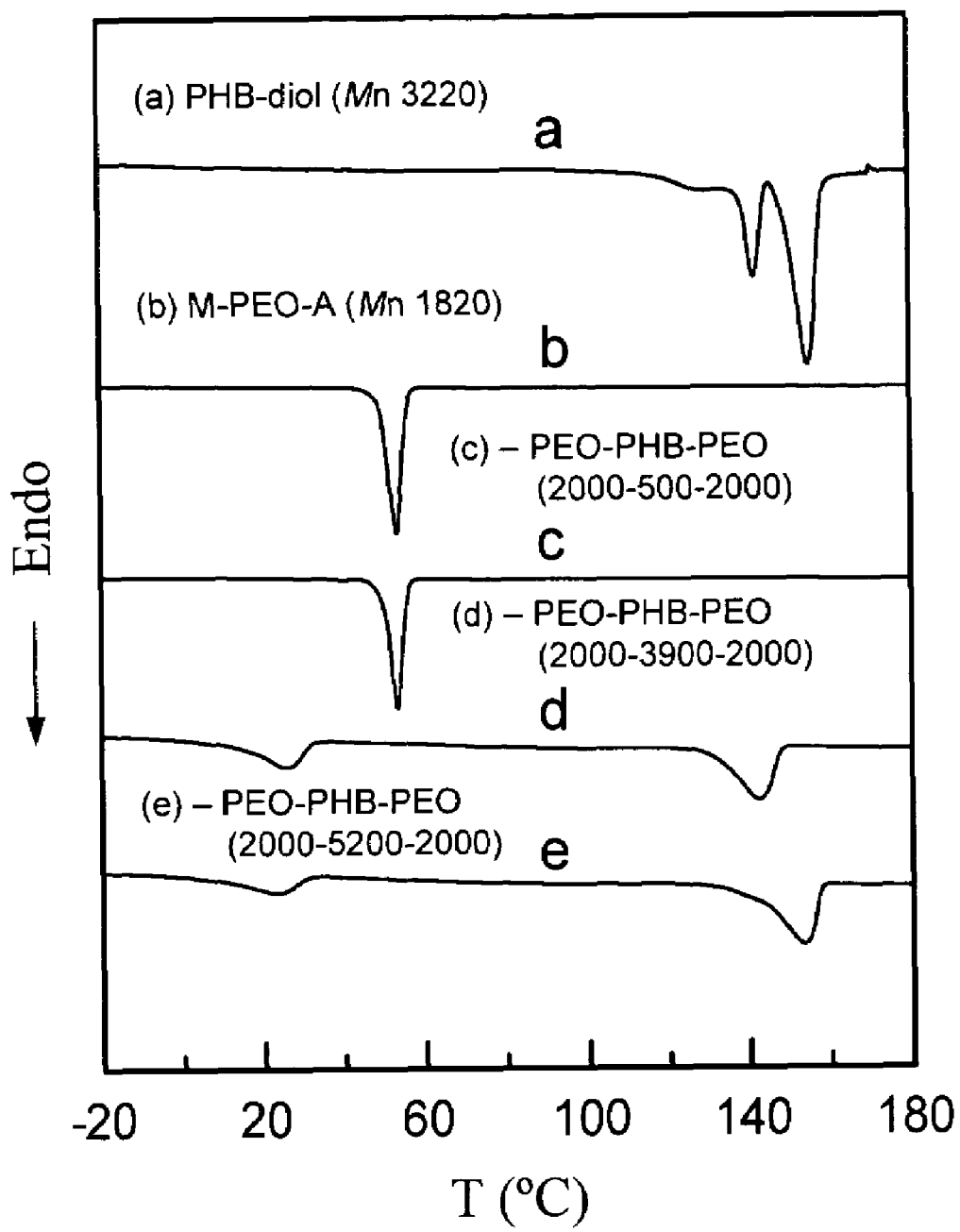
FIGS. 6 and 7 provide differential scanning calorimetry (DSC) thermograms for PEO-PHB-PEO copolymers of different molecular weights, produced in accordance with the process of Example 1, and for the corresponding prepolymers.
Figure 7:
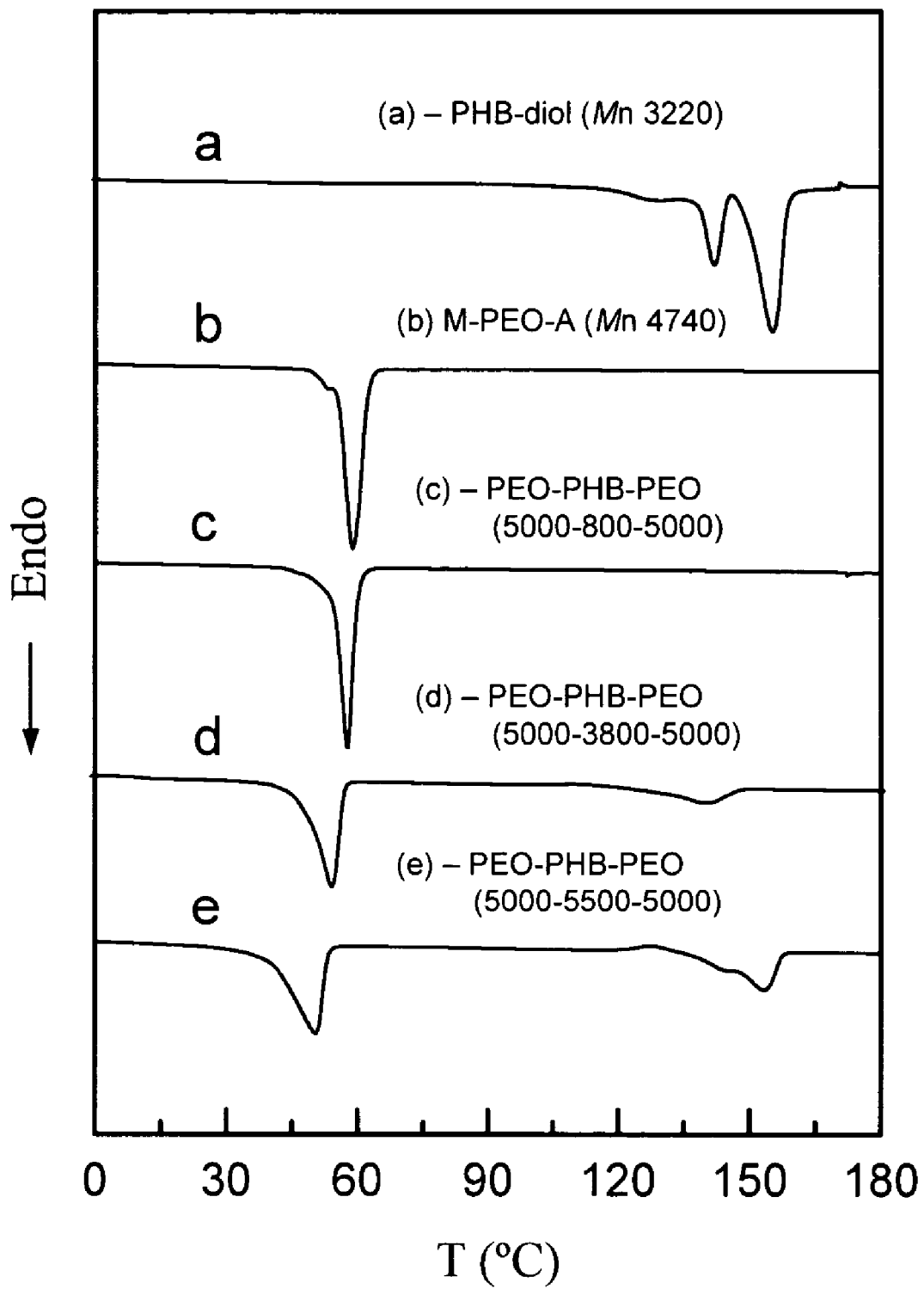

Differential scanning calorimetry (DSC) and wide-angle X-ray diffraction (XRD) studies were carried out to obtain information on the microphase separation and crystallization of the PEO and PHB blocks in the copolymers. FIGS. 6 and 7 show the DSC thermograms for the PEO and PHB precursors and the PEO-PHB-PEO triblock copolymers with different compositions. In addition, numerical values corresponding to the thermal transitions and the crystallinity of each block are presented in Table 3. Both PEO and PHB are crystalline polymers. For copolymers PEO-PHB-PEO (2000-0500-2000) and PEO-PHB-PEO (5000-0800-5000) with a short PHB block, the PHB melting transition peak was not observed, indicating that the PHB crystalline phase was not formed. The melting transition temperature ($T_m$) of the PHB block decreased with decreases in the PHB block length. The melting enthalpy and the crystallinity of the PHB block significantly increased in the copolymers as compared with the pure PHB-diol, presumably caused by the existence of the soft PEO block. In contrast, PEO blocks in all triblock copolymers had lower melting enthalpy and lower crystallinity as compared with pure PEO precursors. All the melting temperatures, melting enthalpies and crystallinity of the PEO block decreased with increase in the PHB block length, or the content of PHB in the copolymers. These may be caused by the hard PHB block, which depressed the crystallization of the PEO blocks in the copolymers.

TABLE 3

| Copolymer | Temp (° C.) | Critical Micelle Formation (cmc) (g/L) |
|---|---|---|
| PEO-PHB-PEO (2000-0500-2000) | 23 | $2.0 \times 10^{-1}$ |
| PEO-PHB-PEO (5000-0800-5000) | 23 | $4.0 \times 10^{-2}$ |
| PEO-PHB-PEO (5000-3800-5000) | 23 | $1.3 \times 10^{-2}$ |

Figure 8:
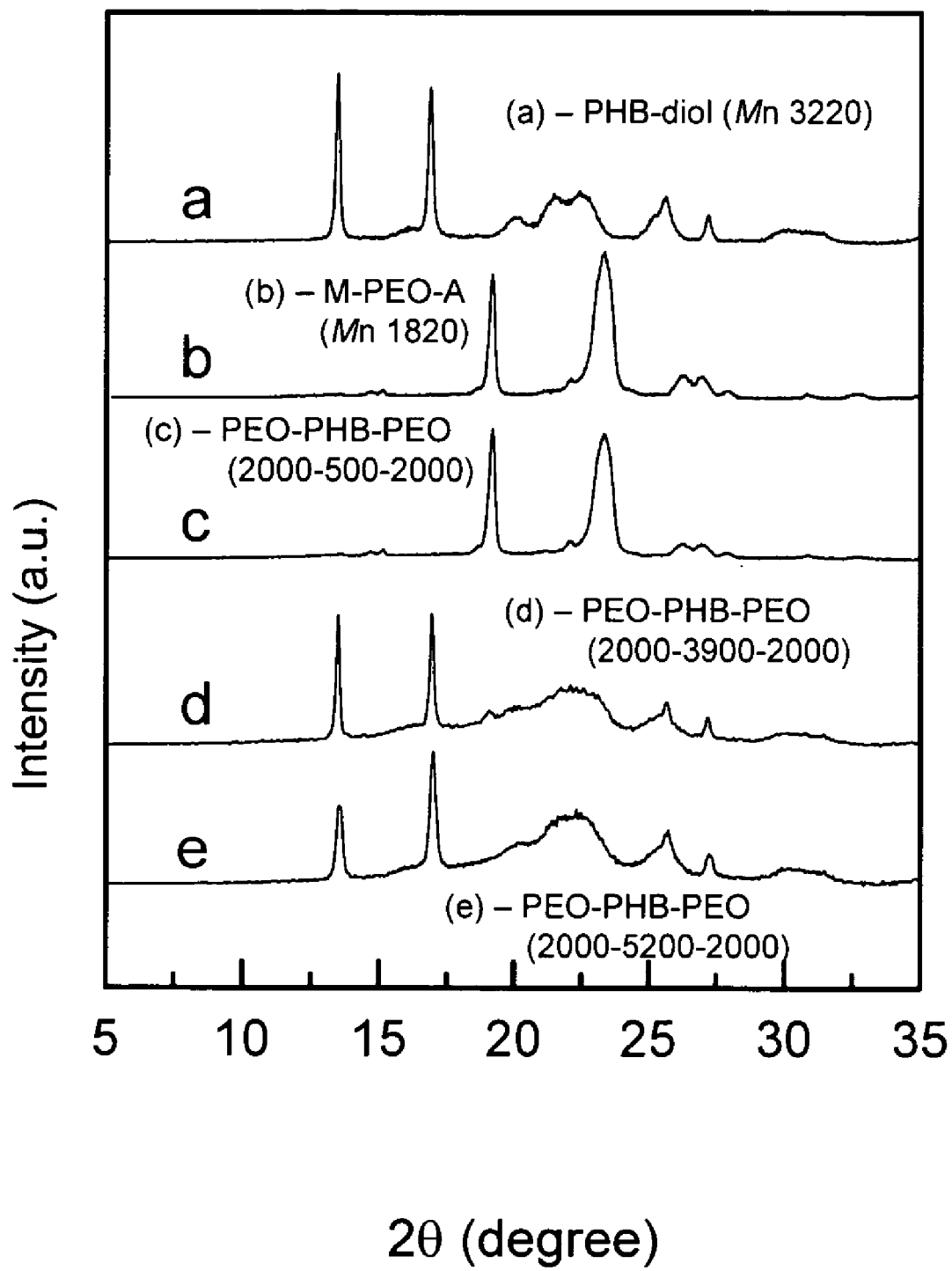
FIGS. 8 and 9 provide wide-angle X-ray diffraction (XRD) diagrams for PEO-PHB-PEO copolymers of different molecular weights, produced in accordance with the process of Example 1, and for the corresponding prepolymers.
Figure 9:
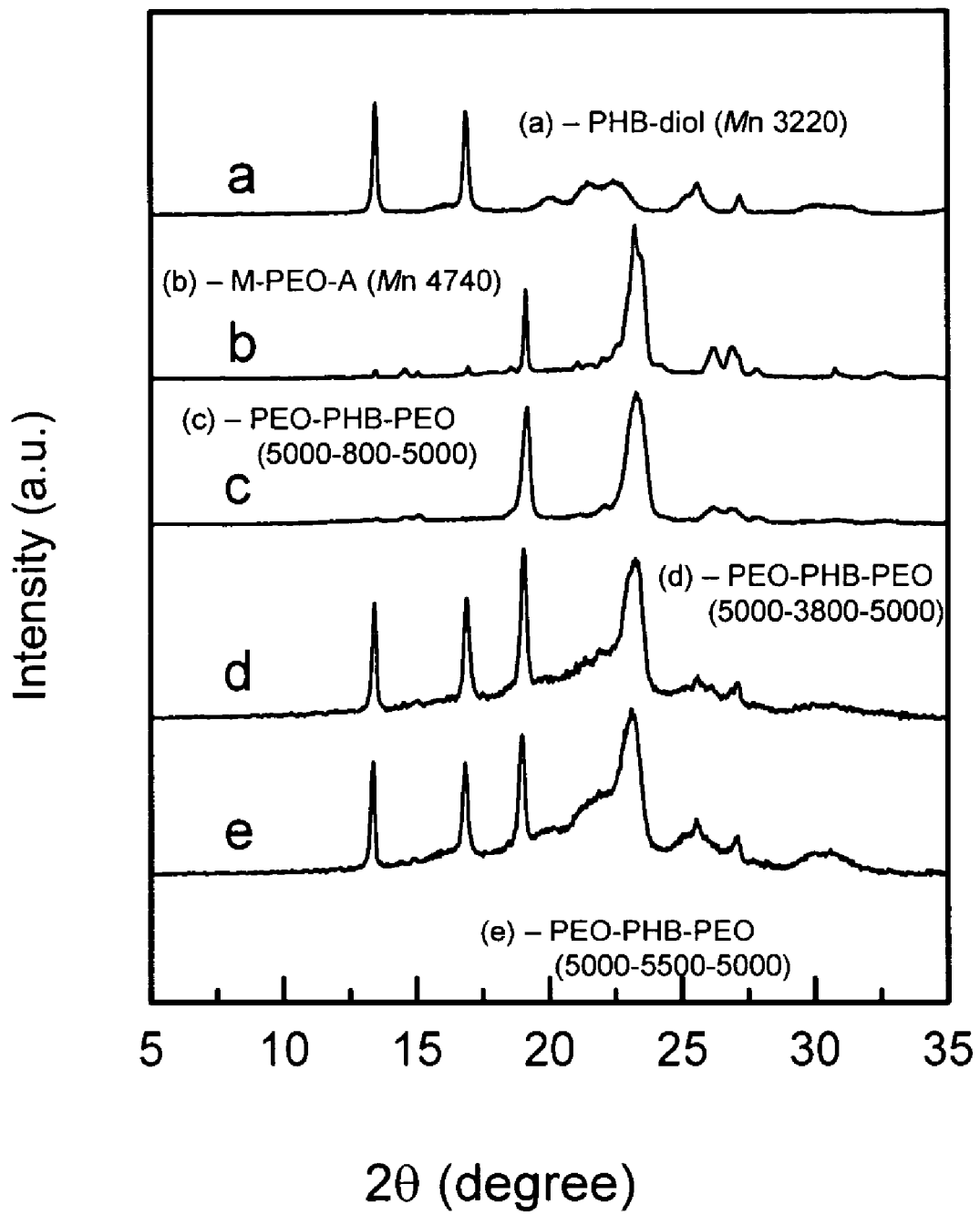

FIGS. 8 and 9 show the XRD diagrams for the PEO and PHB precursors and the PEO-PHB-PEO triblock copolymers synthesized in this work. The reflection peaks for the PHB block did not appear in the diagrams for copolymers with short PHB segments (FIGS. 8c and 9c), indicating that the PHB crystalline phase was not formed. For copolymers with longer PHB segments, the PHB block formed a separated crystalline phase similar to its precursor PHB-diol. The reflection peaks for PEO blocks indicate that the PEO crystalline phase in the copolymer presents a similar structure to its homopolymer. The PEO reflection peaks did not appear for PEO-PHB-PEO (2000-3800-2000) and PEO-PHB-PEO (2000-5500-2000), because their melting temperatures for the PEO blocks were about the ambient temperature (see Table 2 above) at which the XRD was measured. The XRD results are in good agreement with the DSC measurements.

e. Micelle Formation of PEO-PHB-PEO Triblock Copolymers

Triblock copolymers with lower PHB contents, such as PEO-PHB-PEO (2000-0500-2000), PEO-PHB-PEO (5000-0800-5000) and PEO-PHB-PEO (5000-3800-5000), are water-soluble. They may form micelles in aqueous solutions at low concentrations, which was confirmed by dye solubility experiments. The driving force of the micelle formation is thought to be the strong hydrophobic interactions between the PHB blocks. The critical micelle concentrations (cmc) of the block copolymers in aqueous solutions were determined by fluorescence technique using pyrene as a probe. Table 3 lists the cmc values for the three water-soluble triblock copolymers at room temperature. It was found that the cmc strongly depends on the PHB block length in the copolymers, i.e., copolymers with longer PHB block have much lower cmc because the PHB block strongly tends to aggregate in aqueous solution.

Example 2

Triblock Copolymer and Cyclodextrin Complexation and Release Kinetics a. Formation of Inclusion Complexes The reaction scheme of FIG. 1 for synthesis of PEO-PHB-PEO triblock copolymers was again followed. Briefly, high molecular weight PHB was first converted into PHB-diols with lower molecular weights. The PHB-diols were then coupled with PEO-monocarboxylic acid (Mr 5000) to yield the PEO-PHB-PEO triblock copolymers. Two triblock copolymers PEO-PHB-PEO (5000-2300-5000) and PEO-PHB-PEO (5000-3850-5000) were prepared and characterized by NMR, GPC, FI-IR, and DSC. Both copolymers are water-soluble at room temperature. They form micelles in aqueous solutions at low concentrations, which was confirmed by dye solubility experiments using 1,3,5-diphenylhexatriene and pyrene. The driving force of the micelle formation is believed to derive from the strong hydrophobic interactions between the PHB blocks.

Despite the formation of micelles, solutions of 10 wt % of both polymers in water remained clear with good fluidity. Upon addition of 9.7 wt % of α-CD to either polymer solution, gelation occurred at room temperature. Compared to other homo-PEOs, gelation could be induced at lower concentrations with this copolymer. While not wishing to be limited by theory, it is postulated that the inclusion complexes formed by α-CD and PEO blocks of PEO-PHB-PEO triblock copolymers aggregate into microcrystals, which act as physical crosslinks and induce formation of a supramolecular polymer network, consequently leading to the formation of a hydrogel. The micellization of the PHB block is believed to play an important role in the gelation of the copolymer and α-CD solutions. The hydrophobic interactions between the PHB blocks facilitate the formation of the polymer network. Therefore, the driving force for the gelation of PEO-PHB-PEO triblock copolymers and α-CD in aqueous solutions is believed to be a combination of the inclusion complexation between α-CD and PEO blocks and the micellization of the PHB block of the triblock copolymers.

The inclusion complex formation between PEO blocks of the PEO-PHB-PEO copolymers and α-CD in the hydrogels was confirmed by wide-angle X-ray diffraction studies of the hydrogels. The diffractograms of the hydrogels show the pattern for the α-CD-PEO complex, with a number of sharp reflections and a primary one at 2θ=19.4° (d=4.57 Å), representing the channel type structure of crystalline necklace-like complex of α-CD and PEO. Li J., et al., *Macromolecules* 34:7236 (2001); Li J. et al., *Macromolecules* 34:8829 (2001). This pattern suggests the existence of the inclusion complex of α-CD and the PEO blocks. The pattern of solid PEO-PHB-PEG shows two sharp reflections at 13.7° (d=6.46 Å) and 17.2° (d=5.16 Å), which are from the PHB crystalline phase. Interestingly, the pattern for the PHB crystalline phase also appears in the diagram of α-CD-PEO-PHB-PEO (5000-3850-5000) hydrogel, although it is weak. It should be noted that the X-ray diffractogram for a 10 weight % aqueous solution of PEO-PHB-PEO (5000-3850-5000) shows no sharp reflection peaks. The results suggest that the supramolecular system became more highly ordered, and the self-assembly of α-CD complexes with PEO blocks enhanced the aggregation of the PHB blocks.

b. Release Kinetics

Figure 10:
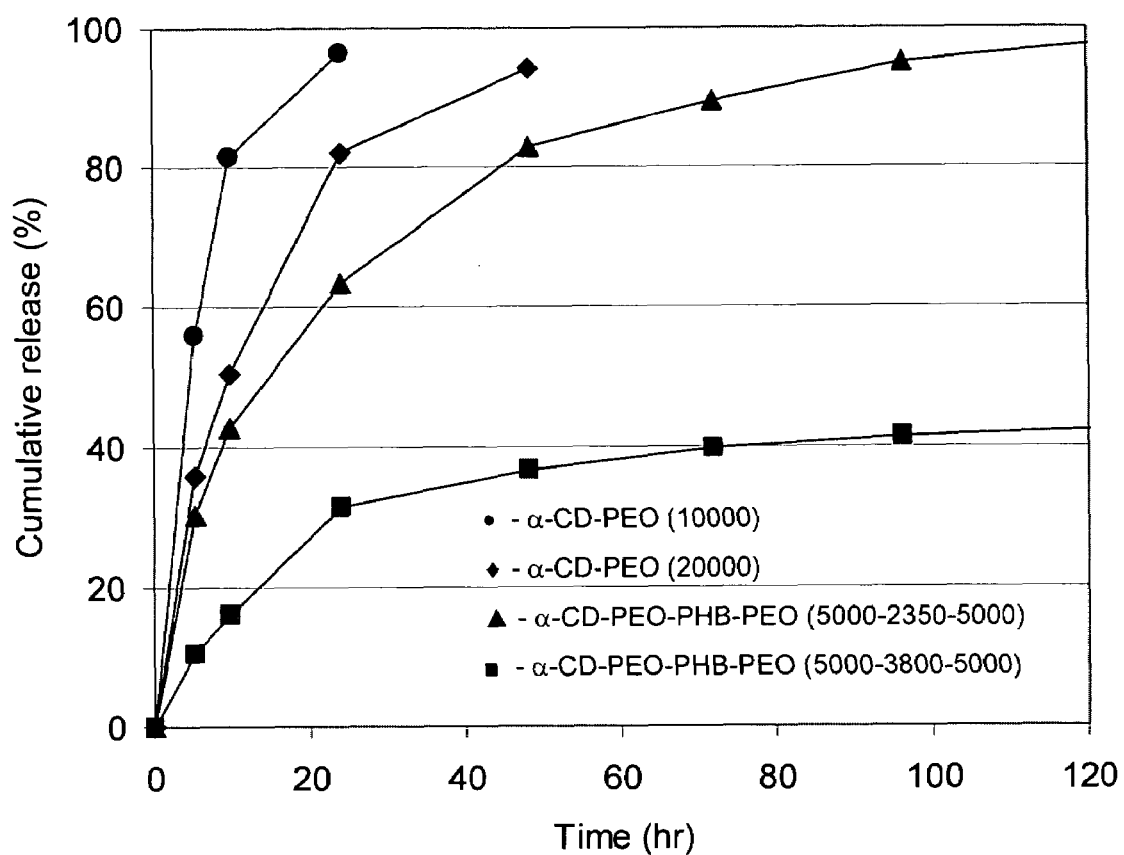
FIG. 10 illustrates in vitro release profiles from Example 2 for BSA-FITC (300 mg of hydrogel loaded with 1.0 mg of BSA-FITC) released from: α-CD-PEO (10000) hydrogel (●) (PRIOR ART); α-CD-PEO (20000) hydrogel (♦) (PRIOR ART); α-CD-PEO-PHB-PEO (5000-2350-5000) hydrogel (▲) in accordance with an embodiment of the present invention; and α-CD-PEO-PHB-PEO (5000-3850-5000) hydrogel (■) in accordance with an embodiment of the present invention.

To demonstrate the stability and delivery characteristics of these hydrogels, the in vitro release of fluorescein isothiocyanate labeled bovine serum albumin (BSA-FITC, molecular weight 67,000) as a model protein drug was studied (FIG. 10). The release characteristics of the α-CD-PEO-PHB-PEO hydrogel of the present invention was compared with that of known (prior art) α-CD-PEO homopolymer hydrogels. The α-CD-PEO homopolymer hydrogel, even with a PEO Mr of 20,000, dissolved in phosphate buffered saline (PBS) within two days. In contrast, the α-CD-PEO-PHB-PEO hydrogels could show sustained release kinetics for BSA-FITC. Interestingly, a small difference in molecular weight, only 1500 Mr, of the PHB block caused a remarkable decrease in the release rate. The α-CD-PEO-PHB-PEO (5000-2350-5000) sustained the release for 4 days, while the α-CD-PEO-PHB-PEO (5000-3850-5000) sustained the release for a longer period in excess of 5 days. No significant release of BSA-FITC occurred after two weeks. These results indicate that the properties of the supramolecular hydrogels of the present invention can be fine-tuned with different copolymers, opening up a wide range of applications. Some PEGylated protein drugs can also be the active component, and the PEO chains may be involved in the complexation with α-CD, which might further improve the controlled release properties of the formulations. A further study of the rheological properties of the hydrogels shows that the gels are thixotropic, i.e., the viscosity of the hydrogels diminished as they were sheared, rendering the controlled release formulations injectable through needles.

Example 3

Hydrogel Release Kinetics for Alternate Model Drug a. Preparation of α-CD-PEO-PHB-PEO Hydrogels A copolymer solution or gel was prepared by first adding 0.090 grams of PBS into 0.060 grams of the triblock PEO-PHB-PEO copolymer, synthesized in accordance with the procedures of Example 1, in a 0.6 mL cuvette. Then 0.30 grams of PBS solution containing 14.5% of α-CD and 0.5% of dextran-FITC (molecular weight 20,000) was added into the PBS-copolymer mixture in the cuvette. The solutions were mixed thoroughly, and then allowed to stand at room temperature overnight. The mixture formed a hydrogel in the cuvette, and then its in vitro release kinetics were studied as further described below. This procedure was carried out once using PEO-PHB-PEO (5000-5500-5000) copolymer and once using PEO-PHB-PEO (5000-3800-5000) copolymer.

b. Preparation of Pure PEO-PHB-PEO Hydrogels

A copolymer solution or gel was prepared by adding 0.090 grams of PBS into 0.060 grams of the triblock PEO-PHB-PEO copolymer, synthesized in accordance with the procedures of Example 1, in a 0.6 mL cuvette. Then 0.30 grams of PBS solution containing 0.5% of dextran-FITC (molecular weight 20,000) was added into the PBS-copolymer mixture in the cuvette. The solutions were mixed thoroughly, and then allowed to stand at room temperature overnight. The mixture formed a hydrogel in the cuvette, and then its in vitro release kinetics were studied as further described below. This procedure was carried out once using PEO-PHB-PEO (5000-5500-5000) copolymer and once using PEO-PHB-PEO (5000-3800-5000) copolymer.

c. Release Kinetics

For in vitro release kinetics studies, each cuvette containing the respective hydrogel including dextran-FITC was placed upside down in a test tube with 12 mL of PBS and incubated in a 37° C. water bath. The PBS was changed at pre-determined intervals of time. The concentration of dextran-FITC released at each interval was analyzed using a fluorescence micro-plate reader.

Figure 11:
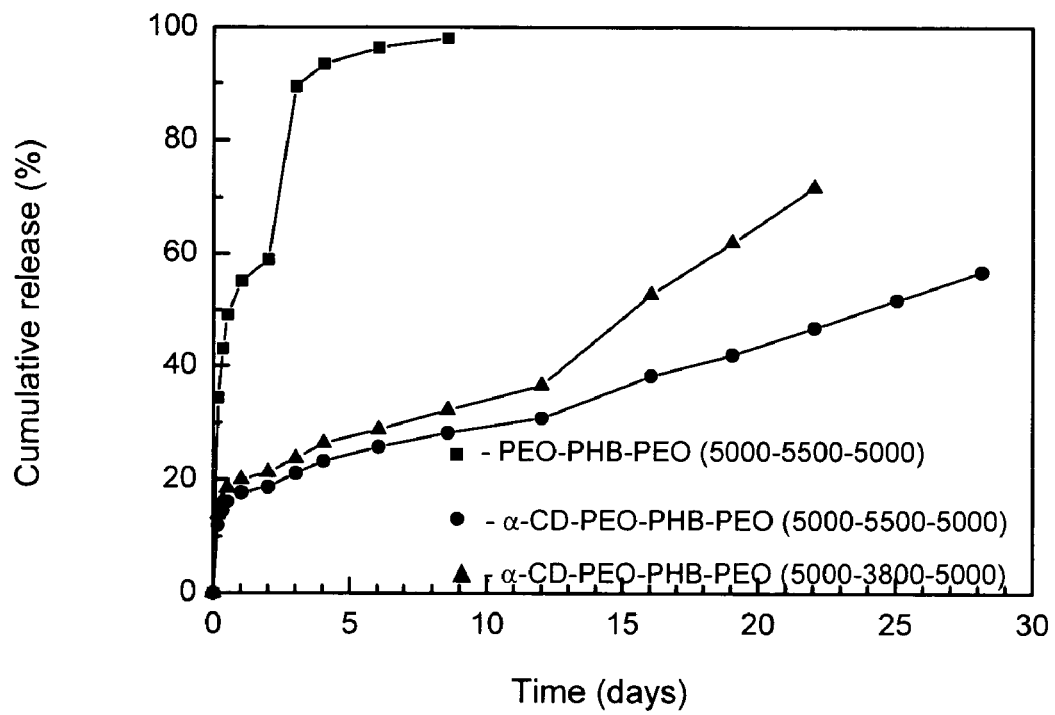
FIG. 11 illustrates in vitro release profiles from Example 3 for dextran-FITC (300 mg of hydrogel loaded with 1.0 mg of dextran-FITC, Mn of 20,000) released from: PEO-PHB-PEO (5000-5500-5000) hydrogel (■); α-CD-PEO-PHB-PEO (5000-5500-5000) hydrogel (●) in accordance with an embodiment of the present invention; and α-CD-PEO-PHB-PEO (5000-3800-5000) hydrogel (▲) in accordance with an embodiment of the present invention.

When following the above procedures, it was found that PEO-PHB-PEO (5000-5500-5000) formed a hydrogel either with or without α-CD. PEO-PHB-PEO (5000-3800-5000) formed a hydrogel only with α-CD, and the solution of PEO-PHB-PEO (5000-3800-5000) without α-CD remained a clear solution that is believed to be unsuitable for sustained release of drugs. FIG. 11 shows the in vitro release profiles of dextran-FITC from the hydrogels. Both α-CD-PEO-PHB-PEO (5000-5500-5000) and α-CD-PEO-PHB-PEO (5000-3800-5000) hydrogels demonstrated sustained release of dextran-FITC for over a few weeks, while the pure PEO-PHB-PEO (5000-5500-5000) hydrogel released dextran-FITC for less than one week. The results indicate that α-CD not only aids the gelation of the PEO-PHB-PEO triblock copolymers, but also forms more stable hydrogels with the triblock copolymers for sustained release of drugs up to multiple weeks. The α-CD-PEO-PHB-PEO (5000-5500-5000) hydrogel exhibited a slower release rate than α-CD-PEO-PHB-PEO (5000-3800-5000) hydrogel, indicating that the properties of the supramolecular hydrogels can be fine-tuned in accordance with the present invention by using different PHB lengths.

Example 4

Inclusion Complex Formation using α- and γ-Cyclodextrins

As noted above, cyclodextrins (CDs) are cyclic molecules consisting of six to eight glucose units joined by α-1,4-glycosidic linkages, and are named α-, β- and γ-CD, respectively. CDs have doughnut-shaped geometries, defining hydrophobic cavities. Although the depths of the hydrophobic cavities of CDs are the same (ca. 7.0 Å), the internal diameters of the cavities are different, being ca. 4.5 Å for α-, ca. 7.0 Å for β-, and ca. 8.5 Å for γ-CD. Bender, M. et al., *Cyclodextrin Chemistry*, Springer-Verlag: Berlin (1978). It has been found that the correlation between the cross-sectional areas of the polymer chains and the cavity sizes of CDs plays an important role in the IC formation. See, e.g., Harada, A. et al., *Nature* 370:126 (1994). In the experiments described herein below, inclusion complexes (ICs) between PEO-PHB-PEO triblock copolymers and α-CD or γ-CD were prepared and characterized to demonstrate their usefulness in forming the hydrogels of the present invention. These experiments demonstrate that both α-CD and γ-CD preferentially include the PEO block, while the center PHB block is only partially covered by CD molecules.

a. Preparation of Inclusion Complexes

PEO-PHB-PEO triblock copolymer was prepared using the procedure of Example 1 above. The molecular characteristics of the triblock copolymers prepared for this experiment are provided in Table 4. PEO-PHB-PEO triblock polymer (20 mg) was soaked with 0.06 mL of $H_2O$ overnight at room temperature. Then, 3.0 mL of a saturated aqueous solution of either α-CD or γ-CD was added, and each mixture was sonicated in a water bath for 10 min, followed by standing for 2 days at room temperature. The precipitated product was collected by centrifugation, and then was washed alternately with water and acetone. Finally, the product was dried in a vacuum at 70° C. for 2 weeks.

TABLE 4

| Copolymer | Mn[a] | Mw[a] | Mw/Mn[a] | Block length (Mn) PEO[a] | Block length (Mn) PHB[b] | $T_m$ (C)[c] PEO | $T_m$ (C)[c] PHB |
|---|---|---|---|---|---|---|---|
| PEO-PHB-PEO (2000-3900-2000) | 7290 | 8000 | 1.10 | 1820 | 3910 | 25.4 | 142.3 |
| PEO-PHB-PEO (2000-5200-2000) | 8120 | 9260 | 1.14 | 1820 | 5230 | 23.3 | 153.6 |
| PEO-PHB-PEO (2000-6800-2000) | 9690 | 11770 | 1.21 | 1820 | 6840 | 25.3 | 155.2 |

[a]Determined by GPC.
[b]Determined by $^1$H NMR and GPC results.
[c]Determined in DSC second heating-up run.

b. Measurements

X-ray diffraction (XRD) measurements were carried out using a Siemens D5005 Diffractometer and Ni-filtered Cu $K_\alpha$ (1.540 51 Å) radiation (40 kV, 40 mA). Powder samples were mounted on a sample holder and scanned in 0.01° steps from 5° to 35° (in 2θ) with 1 second per step.

Differential scanning calorimetry (DSC) measurements were performed using a TA Instruments 2920 differential scanning calorimeter equipped with an auto-cool accessory and calibrated using indium. The following protocol was used for each sample: heating from room temperature to 200° C. at 20° C. min$^-$, holding at 200° C. for 2 min, cooling from 200° C. to −30° C. at 5° C. min$^-$, and finally reheating from −30° C. to 200° C. at 5° C. min$^-$. Data were collected during the second heating run. Transition temperatures were taken as peak maxima. Thermogravimetric analyses (TGA) were made using a TA Instrument SDT 2960. Samples were heated at 20° C. min$^-$ from room temperature to 800° C. in a dynamic nitrogen atmosphere (flow rate=70 ml min$^-$).

$^1$H NMR spectra of the complexes were recorded at 400 MHz on a Bruker DPX-400 NMR spectrometer. Chemical shifts of the complexes were referenced to δ=2.50 ppm for DMSO. $^{13}$C CP/MAS NMR spectra were acquired on a Bruker DPX-400 NMR spectrometer with a sample spinning rate of 8.0 kHz at room temperature. The spectra were acquired with a 2.75 μs proton 90° pulse, a 3 millisecond contact time, and a 3 second repetition time.

Fourier transform infrared (FTIR) spectra were recorded on a Bio-Rad 165 FTIR spectrophotometer; 64 scans were signal-averaged with a resolution of 2 cm$^{-1}$ at room temperature. Samples were prepared by dispersing the complexes in KBr and compressing the mixtures to form disks.

c. Results and Discussion

When an aqueous solution of α-CD or γ-CD was added to the PEO-PHB-PEO triblock copolymer soaked with water and sonicated for 10 minutes, complexes were formed as crystalline precipitates. The appearance of precipitates was an indication of the formation of crystalline inclusion complexes (ICs) between the copolymers and CDs. Harada, A. et al., *Macromolecules*, 26:5698 (1993). In comparison, there was no precipitate formed in the mixture of β-CD and the PEO-PHB-PEO triblock copolymer solution even after standing 2 weeks. This observation indicates that the PEO-PHB-PEO triblock polymers can form ICs with α-CD and γ-CD, but may not be able to with β-CD. The yields of the IC formation are shown in Table 5.

TABLE 5

| Copolymer | Yield (mg) α | Yield (mg) γ | CH$_2$CH$_2$O/CD α | CH$_2$CH$_2$O/CD γ |
|---|---|---|---|---|
| PEO-PHB-PEO (2000-3900-2000) | 75.0 | 60.6 | 1.2 | 2.1 |
| PEO-PHB-PEO (2000-5200-2000) | 67.9 | 56.3 | 1.4 | 2.6 |
| PEO-PHB-PEO (2000-6800-2000) | 65.8 | 60.0 | 1.1 | 2.3 |

Figure 12:
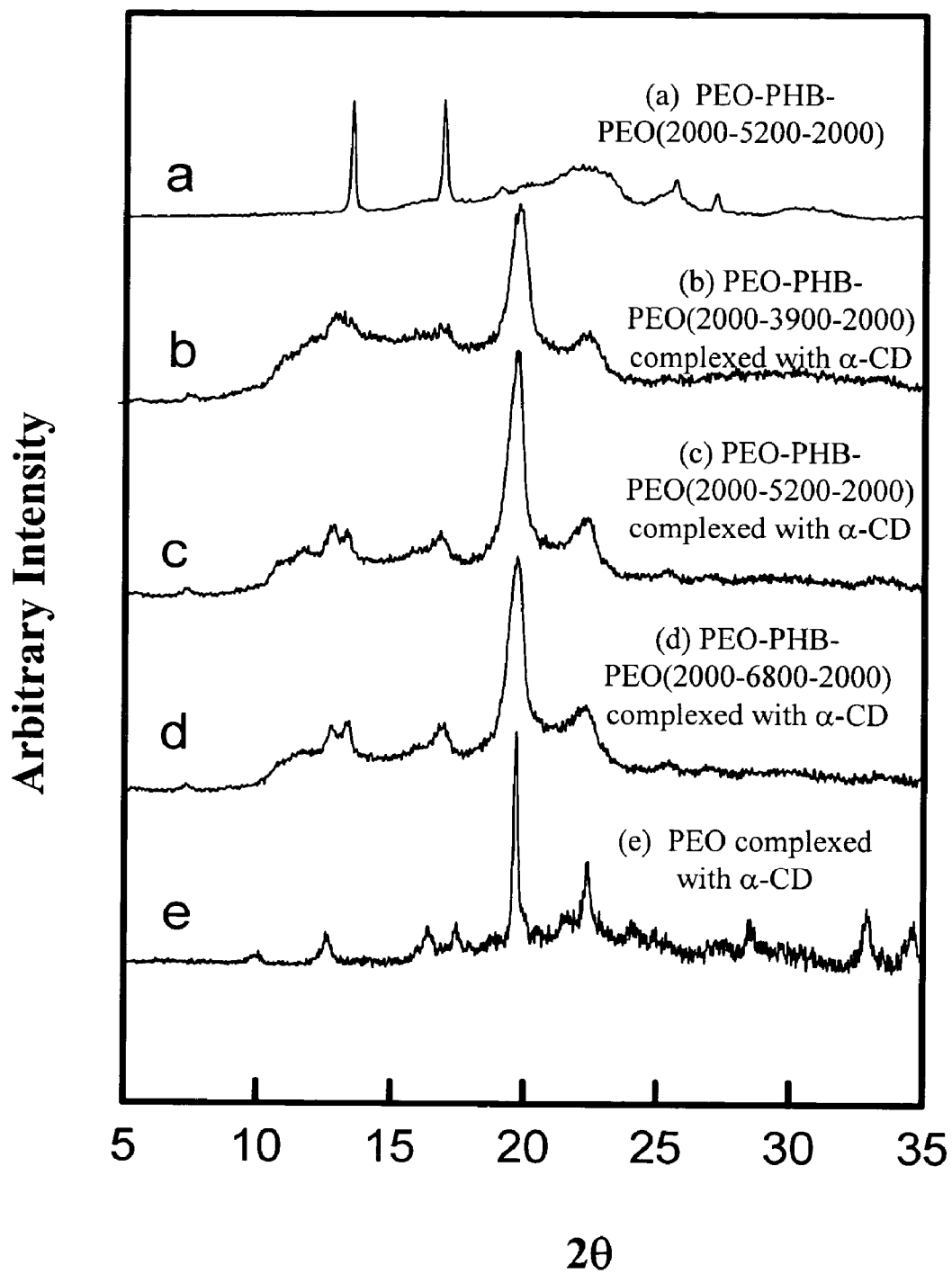
FIGS. 12 and 13 provide XRD diagrams for uncomplexed PEO-PHB-PEO copolymer compared with PEO-PHB-PEO copolymers of various molecular weights complexed with either α-CD (FIG. 12) or γ-CD (FIG. 13)

The formation of CD-PEO-PHB-PEO ICs was strongly supported by X-ray diffraction (XRD) studies. FIG. 12 shows the XRD patterns of pure PEO-PHB-PEO (2000-5200-2000), and ICs of α-CD with all three PEO-PHB-PEO triblock copolymers in comparison with IC formed by α-CD and PEO (Mn 2000). In FIG. 12e, a number of sharp reflections with two prominent peaks at 2θ=19.4° and 22.1° represent the channel type structure of a crystalline necklace-like complex of α-CD and PEO. See, e.g., Takeo, K. et al., *Agric. Biol. Chem.*, 34:1787 (1970). The observation of similar diffraction patterns for α-CD-PEO-PHB-PEO ICs (FIG. 12b-d) indicates the α-CD-PEO-PHB-PEO ICs assume the channel type structure like that of α-CD-PEO IC. When compared with α-CD-PEO IC, two extra small peaks at 2θ=13.6° and 17.0° appear in the patterns of α-CD-PEO-PHB-PEO ICs. The relative intensity of the two peaks increases with increasing the ratio of PHB to PEO in PEO-PHB-PEO. With pure PEO-PHB-PEO, as shown in FIG. 12a, the peaks at 13.6° and 17.0° are a characteristic of crystalline PHB. Thus, the presence of the two peaks is believed to indicate that parts of the PHB block aggregate to form a crystalline phase, which coexists with the IC crystals.

Figure 13:
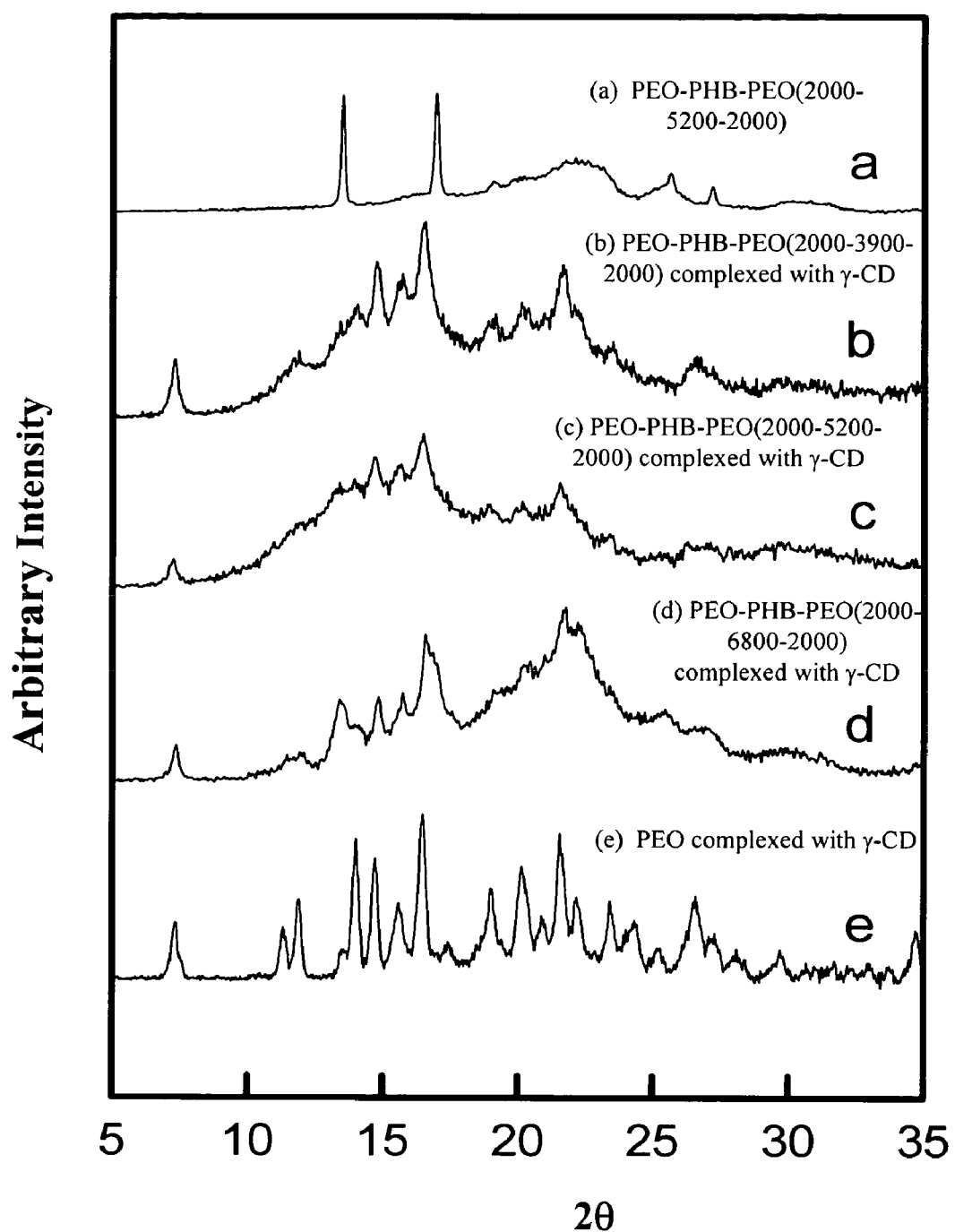

The XRD patterns of γ-CD-PEO-PHB-PEO ICs are shown in FIG. 13, as compared with those of pure PEO-PHB-PEO and γ-CD-PPO ICs. Although the relative intensities of each peak are different, the XRD patterns of γ-CD-PEO-PHB-PEO ICs are very similar to each other and are also similar to that of γ-CD-PPO IC, in which a channel type structure has been established. Furthermore, the characteristic peak at 7.6° is observed, which is the key feature serving as a fingerprint for the channel-type structure of γ-CD-polymer ICs. See, e.g., Harada, A. et al., *Macromolecules*, 29:5611 (1996). Therefore, γ-CD-PEO-PHB-PEO ICs are believed to assume a channel type structure. The two peaks at 2θ=13.6° and 17.0° attributed to the crystalline PHB block are also observed in the XRD patterns of γ-CD-PEO-PHB-PEO ICs as in α-CD-PEO-PHB-PEO ICs. The broadening XRD patterns for α-CD-PEO-PHB-PEO and γ-CD-PEO-PHB-PEO ICs compared with the stoichiometric α-CD-PEO and γ-CD-PPO ICs (FIG. 12e and FIG. 13e) are due to the lower crystallinity of the ICs, most likely caused by the uncovered PHB segments that "break up" and shorten the channels in the ICs.

Figure 14:
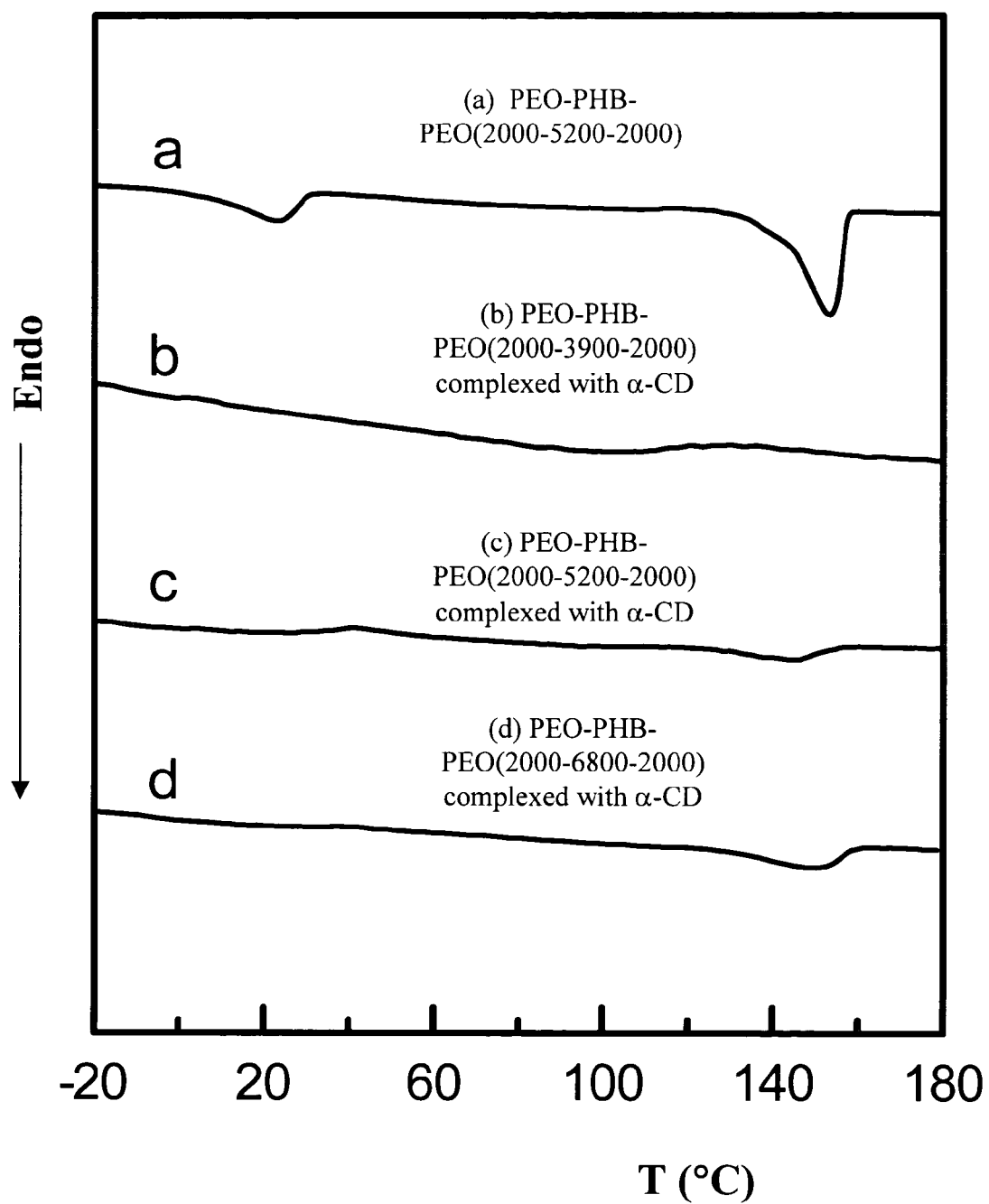
FIGS. 14 and 15 provide DSC thermograms for uncomplexed PEO-PHB-PEO copolymer compared with PEO-PHB-PEO copolymers of various molecular weights complexed with either α-CD (FIG. 14) or γ-CD (FIG. 15)

The DSC curves of pure PEO-PHB-PEO (2000-5200-2000) and α-CD-PEO-PHB-PEO ICs are shown in FIG. 14. As shown in FIG. 14a, there are two endothermic peaks at 23.3° C. and 153.6° C. in the DSC curve of pure PEO-PHB-PEO (2000-5200-2000), corresponding to crystal fusion of PEO and PHB blocks, respectively. Upon formation of ICs, the endothermic peak corresponding to PEO block is absent in FIG. 14b-14d. This is because the PEO block is included separately in the channels of the host α-CD lattice, and then cannot aggregate to form the crystalline phase. However, the endothermic peak corresponding to the PHB block is still observable (FIG. 14b-14d). But the fusion temperatures move to a lower range, and the enthalpy changes result in a dramatic decrease of the α-CD-PEO-PHB-PEO ICs. The results indicate that each PHB block is partially covered by α-CD, and most likely the middle portion of the PHB block is uncomplexed by α-CD. The decreases in fusion temperature and the enthalpy change are due to the perturbation of crystallization resulting from the partial inclusion of the PHB block. Shuai, X. et al. (*Macromolecules*, 35:3778 (2002)) have reported the formation of ICs between poly [(R)-3-hydroxybutyrate] and α-CD in DMSO. Their results showed that a PHB chain was only partially included by α-CD. For the system of the present invention, threading of α-CD onto the PHB block is still thwarted by the hydrophobicity of PHB, although the CD threading onto the PEO block can further slide onto the center PHB block. In the α-CD-PEO-PHB-PEO ICs, both fusion temperature and enthalpy change trend to increase with an increase in the chain length of the middle PHB block. This is because the α-CD-PEO-PHB-PEO ICs with longer PHB block have longer uncomplexed portions of PHB chain.

Figure 15:
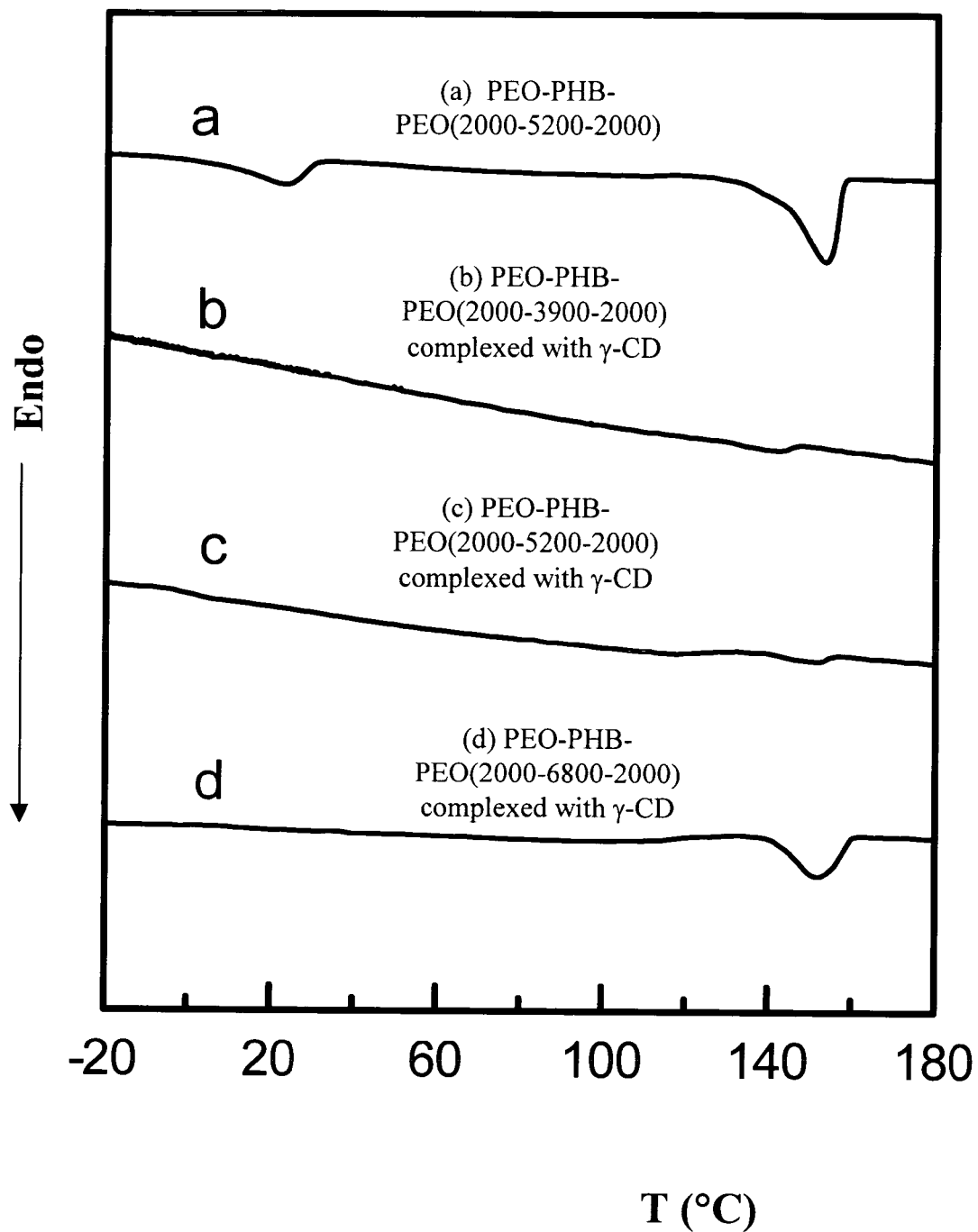

FIG. 15 shows the DSC curves of pure PEO-PHB-PEO (2000-5200-2000) and γ-CD-PEO-PHB-PEO ICs. Similar results as those from FIG. 14 can be obtained. All the DSC results for both α-CD-PEO-PHB-PEO and γ-CD-PEO-PHB-PEO ICs indicate that the PEO block is fully covered by CDs, while the center PHB block is partially covered, which is consistent with the XRD results.

Figure 16:
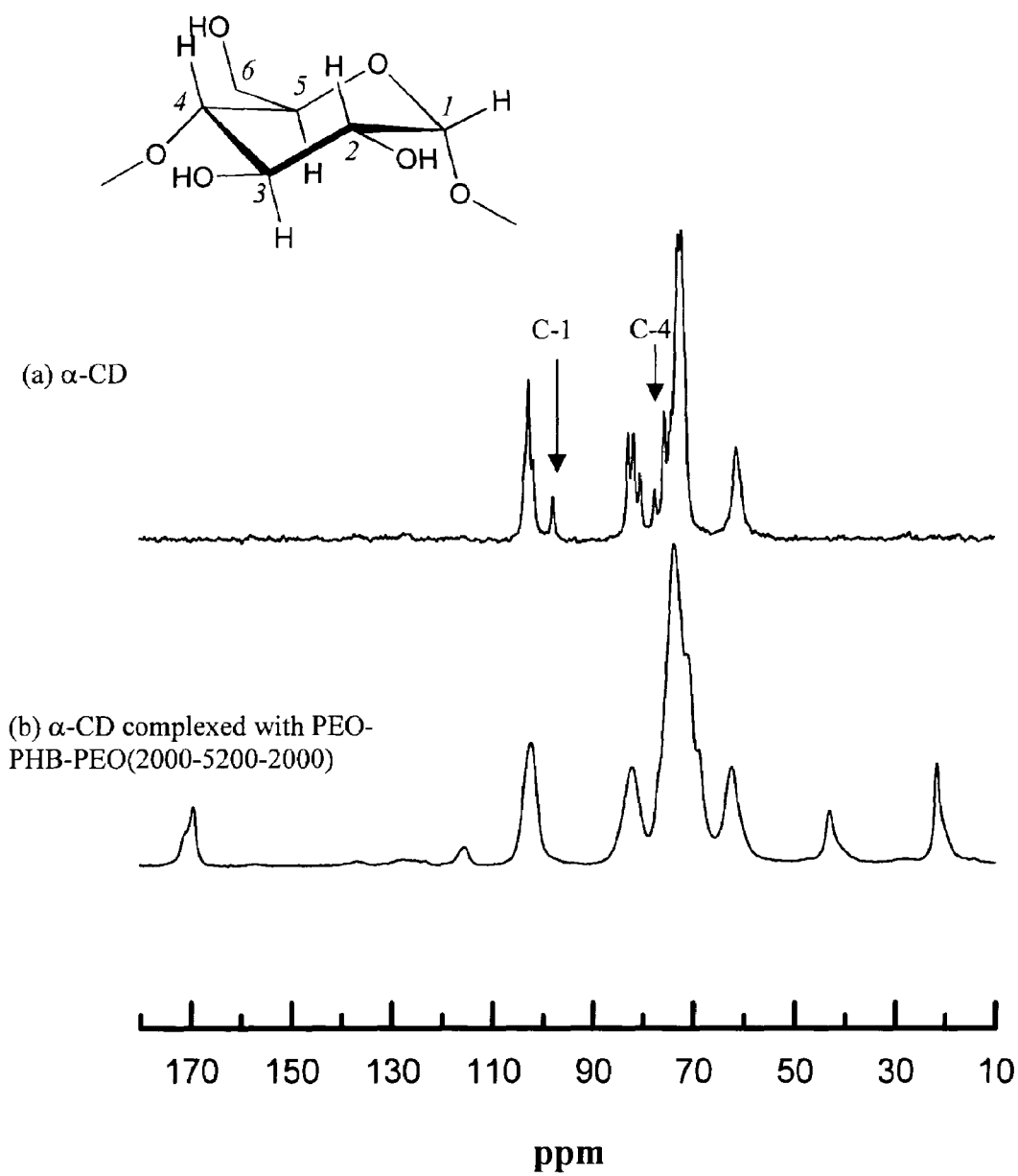
FIG. 16 provides 13C CP/MAS NMR spectra for uncomplexed α-CD and α-CD complexed with PEO-PHB-PEO (2000-5200-2000) copolymer, with arrows showing resolved resonances for C-1 and C-4 adjacent to a single conformationally strained glycosidic linkage.

FIG. 16 shows the $^{13}$C CP/MAS NMR spectra of α-CD and α-CD-PEO-PHB-PEO (2000-5200-2000) ICs. The spectrum of α-CD in the uncomplexed state shows multiple resolved resonances for $C_1$ and $C_4$. Resonances for $C_1$ and $C_4$ adjacent to a single conformationally strained glycosidic linkage are especially observed in the spectrum. The results indicate that the α-CD assumes a less symmetrical conformation in the crystalline uncomplexed state. On the contrary, for α-CD-PEO-PHB-PEO (2000-5200-2000) IC, all $C_1$-$C_6$ of CD show a single unresolved resonance, indicating that α-CD adopts a more symmetric conformation and each glucose unit of α-CD is in a similar environment in the IC.

Figure 17:
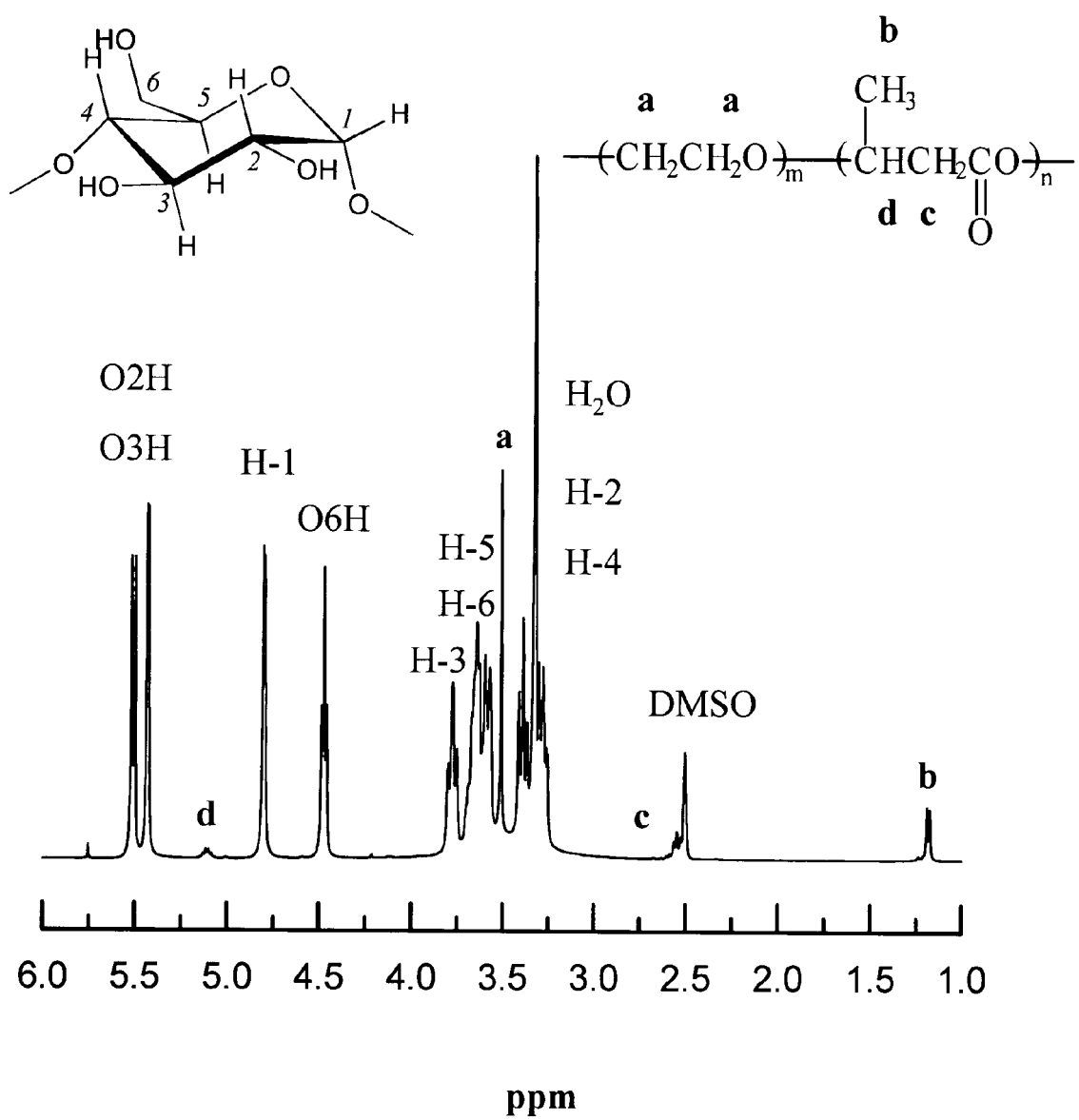
FIG. 17 provides the 400 $^1$H NMR spectrum of α-CD complexed with PEO-PHB-PEO (2000-5200-2000) copolymer in DMSO-$d_6$.

The partial coverage of the center PHB block by α-CD or γ-CD was also demonstrated by the $^1$H NMR spectra of the CD-PEO-PHB-PEO ICs. FIG. 17 shows the $^1$H NMR spectrum of α-CD-PEO-PHB-PEO (2000-5200-2000) in DMSO-$d_6$. As shown in FIG. 17, all proton signals belonging to both α-CD and PEO-PHB-PEO (2000-5200-2000) are confirmed. The ratio of the ingredients in the crystalline IC can be determined by comparing the integral of the peaks. As reported previously, PEO can form inclusion complexes with α-CD and γ-CD, with the ratio of PEO repeat units to CD being 2 and 4, respectively. See, e.g., Harada et al. (1994). However, the ratio of PEO repeat units to α-CD obtained from FIG. 17 for α-CD-PEO-PHB-PEO (2000-5200-2000) IC is 1.4, indicating more α-CD molecules have been contained in the α-CD-PEO-PHB-PEO (2000-5200-2000) IC than forming a stoichiometric complex of α-CD and the PEO blocks. On the other hand, the solid state $^{13}$C CP/MAS NMR measurement shows all α-CD in the IC has been threaded on polymer chain and adapts a channel structure. Thus, some α-CD is believed to slide onto the middle PHB block. The ratios of PEO repeat unit to CD for all tested CD-PEO-PHB-PEO ICs are summarized in Table 5. In the cases of ICs with γ-CD, the ratios are between 2.1 and 2.6, which indicates some γ-CD molecules also slide onto the center PHB block. These results further support the hypothesis that the PEO block is fully covered by α-CD or γ-CD, while the center PHB block is partially covered in the CD-PEO-PHB-PEO ICs.

Figure 18:
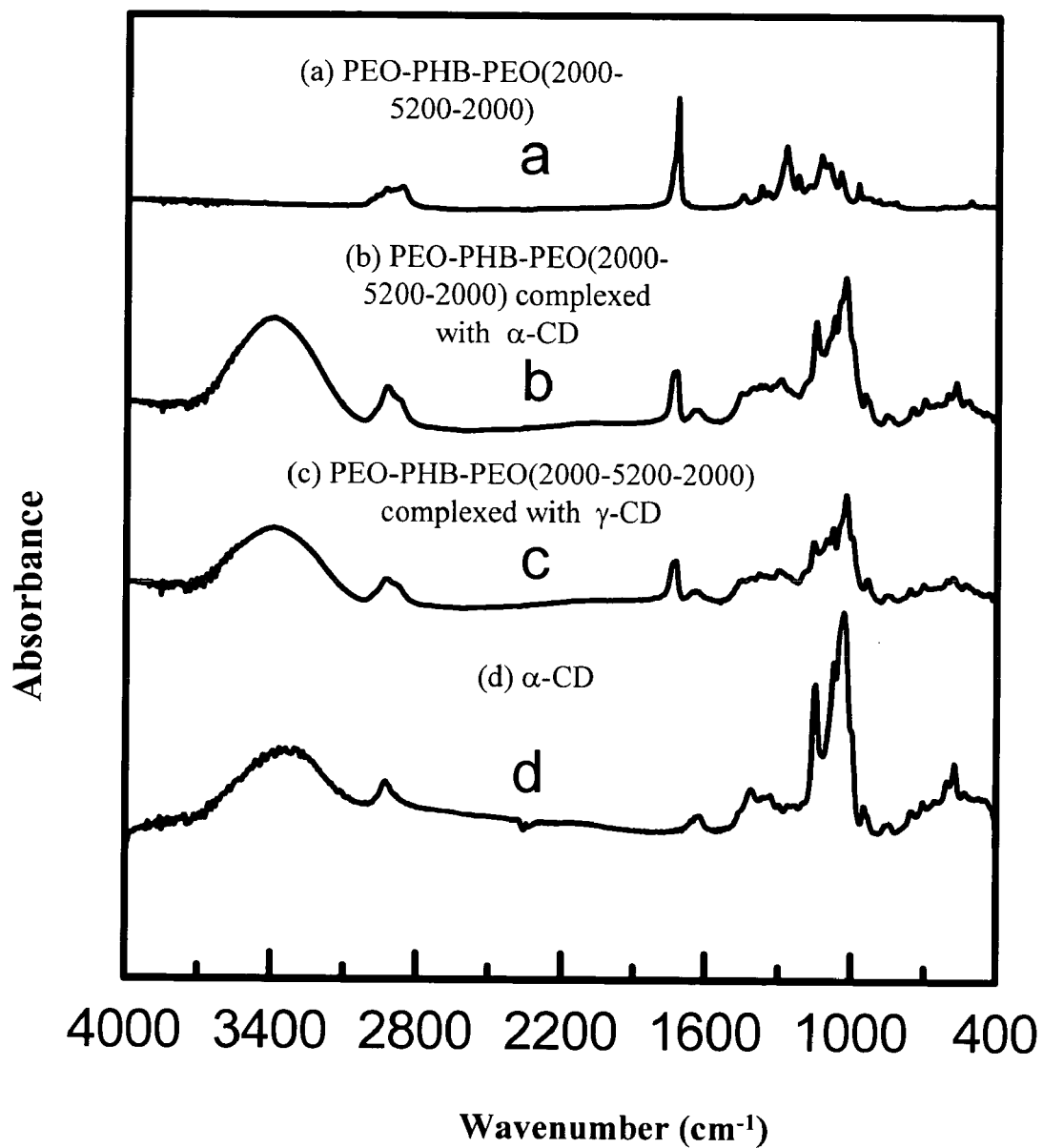
FIGS. 18 and 19 provide FTIR spectra of differing resolution for uncomplexed PEO-PHB-PEO (2000-5200-2000) copolymer compared with this copolymer complexed with either α-CD or γ-CD and compared to pure α-CD.

FIG. 18 shows the FTIR spectra of the α-CD-PEO-PHB-PEO ICs as compared with the pure PEO-PHB-PEO(20-52-20) and α-CD. The spectrum for α-CD shows a broad band at 3360 cm$^{-1}$ due to the symmetric and antisymmetric O—H stretching mode. Upon formation of ICs, the broad hydroxyl band shifts to a higher frequency at 3390 cm$^{-1}$ in the spectra of the ICs (FIGS. 18b and c), most probably due to formation of hydrogen bonds between the hydroxyl groups of CDs in the channel structure. The FTIR spectrum of pure PEO-PHB-PEO (2000-5200-2000) is characterized by an intensive carbonyl stretching band at 1723 cm$^{-1}$ (FIG. 18a), which is ascribed to the PHB part in PEO-PHB-PEO (2000-5200-2000). The carbonyl stretching band is resolved into an intensive band at 1723 cm$^{-1}$ and a weak shoulder at 1736 cm$^{-1}$, corresponding to the carbonyl stretching band of the crystalline PHB phase and that of the amorphous PHB regions, respectively. Ikejima, T., et al., *Macromol. Chem. Phys.*, 200:413 (1999).

Figure 19:
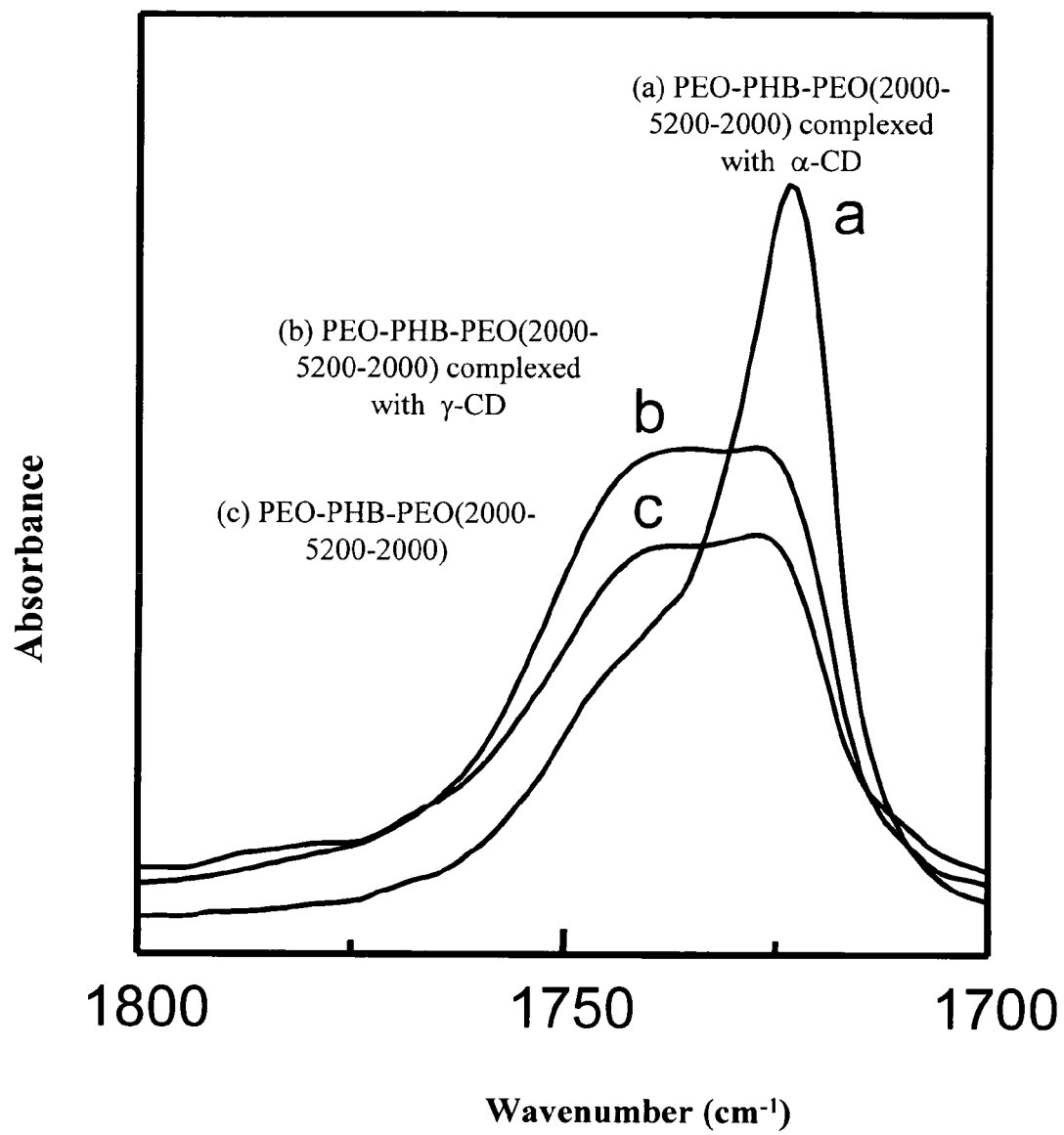

FIG. 19 shows the expansion of the carbonyl stretching region of these FTIR spectra. As compared with the pure PEO-PHB-PEO (2000-5200-2000), the peak at 1723 cm$^{-1}$ decreases sharply while the shoulder at 1736 cm$^{-1}$ increases sharply in the spectra of α-CD-PEO-PHB-PEO (2000-5200-2000) and γ-CD-PEO-PHB-PEO (2000-5200-2000). When ICs are formed, some of the PHB segments are located individually in the IC channels and thus are not able to aggregate to form PHB crystals. The existence of the peak at 1723 cm$^{-1}$ indicates only a portion of the PHB blocks have been covered by CD and the remaining PHB segments still can aggregate to form a crystalline phase. This is in agreement with the XRD and the DSC results discussed above.

Figure 20:
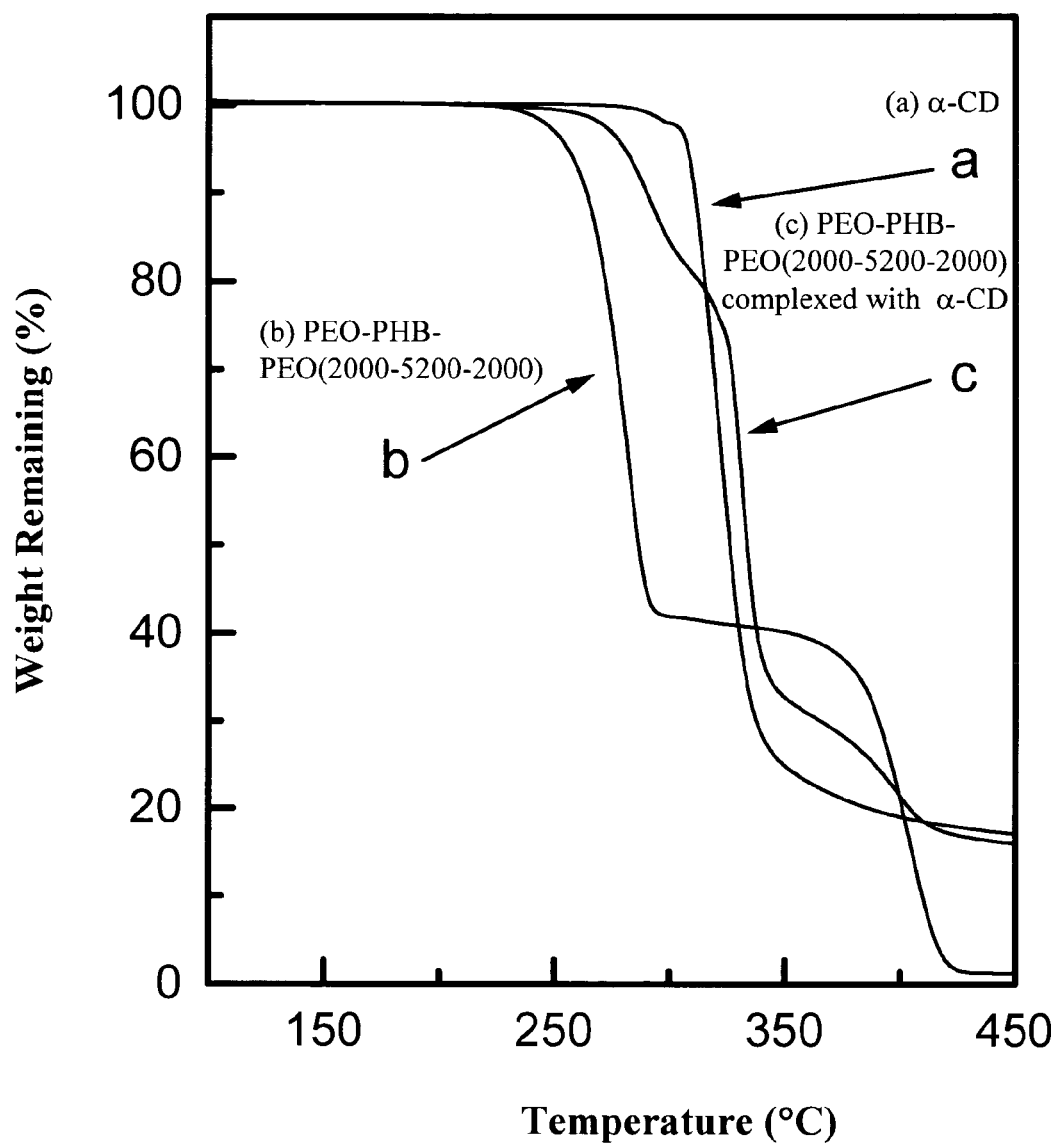
FIG. 20 provides thermogravimetric analysis (TGA) curves of pure α-CD, pure PEO-PHB-PEO (2000-5200-2000) copolymer and the complex of this copolymer with α-CD.

FIG. 20 shows the results of the thermogravimetric analysis (TGA) scans for α-CD, pure PEO-PHB-PEO (2000-5200-2000) and their IC up to 450° C. As shown in FIG. 20, α-CD starts to decompose at 279.2° C. Pure PEO-PHB-PEO (2000-5200-2000) shows an initial weight loss of 58.7% and a second weight loss of 39.3% on heating, with onset of thermal decomposition at 222.4° C. and 243.8° C., respectively. It is believed that the first weight loss is due to decomposition of PHB block and the second weight loss to PEO block. However, the onsets of decomposition of PHB block, PEO block and α-CD in the α-CD-PEO-PHB-PEO IC are observed at 247.2° C., 309.3° C. and 365.8° C., respectively. They all are higher than those of the PHB and PEO blocks in PEO-PHB-PEO (2000-5200-2000) and the pure α-CD, respectively. The higher decomposition temperatures of α-CD-PEO-PHB-PEO ICs are believed to be due to the contribution of complex formation to the thermal stability of both α-CD and PEO-PHB-PEO. The similar results have been also observed for γ-CD-PEO-PHB-PEO ICs.

Example 5

PEO-PHB-PEO Copolymer Micelle Characterization

Micelles were formed in aqueous media from PEO-PHB-PEO copolymer produced in accordance with the overall procedure of Example 1, and then characterized, as follows:

a. Materials

Natural source poly[(R)-3-hydroxybutyrate] (PHB) was purchased from Aldrich. The PHB sample was purified by dissolving in chloroform followed by filtration and precipitation in petroleum ether before use. The $M_n$ and $M_w$ of the purified PHB were $8.7 \times 10^4$ and $2.3 \times 10^5$, respectively. Methoxy-poly(ethylene oxide) monopropionic acid (M-PEO-A) with a molecular weight of ca. 5000 was purchased from Shearwater Polymers, Inc., USA. The $M_n$ and $M_w$ of the M-PEO-A were found to be 4740 and 4880, respectively. Bis(2-methoxyethyl)ether (Diglyme, 99%), ethylene glycol (99%), dibutyltin dilaurate (95%), 1,3-N,N'-dicyclohexylcarbodiimide (DCC, 99%), 4-(dimethylamino)pyridine (DMAP, 99%), succinic anhydride (97%), and triethylamine (99%) were obtained from Aldrich. Diglyme was dried with a molecular sieve, and methylene chloride was distilled from $CaH_2$ before use.

b. Preparation of Pure PEO-PHB-PEO Hydrogels

The telechelic hydroxylated PHB (PHB-diol) prepolymer with low molecular weight was prepared by transesterification from the natural PHB and diethylene glycol with dibutyltin dilaurate as catalyst in diglyme (yield, 80%). The PHB-diol (0.38 g, $1.2 \times 10^{-4}$ mol, $M_n$=3220), M-PEO-A (1.42 g, $3.0 \times 10^{-4}$ mol, $M_n$=4740), and DMAP (12 mg, $9.8 \times 10^{-5}$ mol) were dried in a 50-mL two-neck flask under vacuum at 60° C. (oil bath) over night. Anhydrous methylene chloride (25-30 ml) was added to the flask, and then was removed by distillation (oil bath, 75° C.), to remove any trace water in the system. When the flask cooled down, DCC (0.098 g, $4.7 \times 10^{-4}$ mol) dissolved in 4 mL of anhydrous methylene chloride was added, and the mixture was stirred overnight at room temperature under nitrogen. Precipitated dicyclohexylurea (DCU) was removed by filtration. The polymer was twice precipitating from diethyl ether. The desired triblock copolymer product, redissolved in methanol or chloroform, was further purified by fractionation. Yield: 0.75 g, 56%. GPC (THF): $M_n$=12720, $M_n$ (PHB block) =3820, $M_n$ (PEO block)=4740, $M_w$=13770, $M_w/M_n$=1.08. $T_m$=54° C. (for PEO block) and 140° C. (for PHB block). $^1$H NMR (400 MHz, $CDCl_3$): $\delta$ 5.29 (m, methine H of PHB block), 4.32 (s, —$COOCH_2CH_2COO$—), 3.68 (s, —$CH_2OCH_2$— of PEO block), 3.42 (s, —$OCH_3$ end group), 2.48-2.67 (m, methylene H of PHB block), 1.31 (d, methyl H of PHB block). IR (KBr): 2886, 1723, 1456, 1380, 1280, 1111, 1061, 962, 842, 516 $cm^{-1}$.

c. Polymer Characterization

Gel permeation chromatography (GPC) analysis was carried out with a Shimadzu SCL-10A and LC-8A system equipped with two Phenogel 5µ 50 and 1000 Å columns (size: 300×4.6 mm) in series, and a Shimadzu RID-10A refractive index detector. THF was used as the eluent at a flow rate of 0.30 mL/min at 40° C. Monodispersed poly (ethylene glycol) standards were used to obtain a calibration curve. The $^1$H NMR spectra were recorded on a Bruker AV-400 NMR spectrometer at 400 MHz at room temperature. The $^1$H NMR measurements were carried out with an acquisition time of 3.2 sec, a pulse repetition time of 2.0 sec, a 30° pulse width, 5208-Hz spectral width, and 32 K data points. Chemical shift was referred to the solvent peaks ($\delta$=7.3 ppm for $CHCl_3$).

d. Fluorescence Spectroscopy

Steady-state fluorescence spectra were recorded on a Shimadzu RF-5301PC spectrofluorophotometer. Excitation spectra were monitored at 373 nm. The slit widths for both excitation and emission sides were maintained at 1.5 nm. Sample solutions were prepared by dissolving a predetermined amount of block copolymer in an aqueous pyrene solution of known concentration, and the solutions were allowed to stand for 1 day to equilibrate.

e. Results and Discussion

The micelle formation of the PEO-PHB-PEO triblock copolymer was studied using a dye absorption technique. The critical micelle concentration (cmc) value of the PEO-PHB-PEO triblock copolymer in aqueous solution was determined using fluorescence excitation spectra of pyrene as a probe. Wilhelm, M., et al., *Macromolecules* 24:1033-1040 (1991); Noda, T., et al., *Macromolecules* 33:3694-3704 (2000). This method is based on the shift of the 0-0 absorption maxima for pyrene in water from 334 nm to 337 nm when pyrene is solubilized in a micellar phase.

Figure 21:
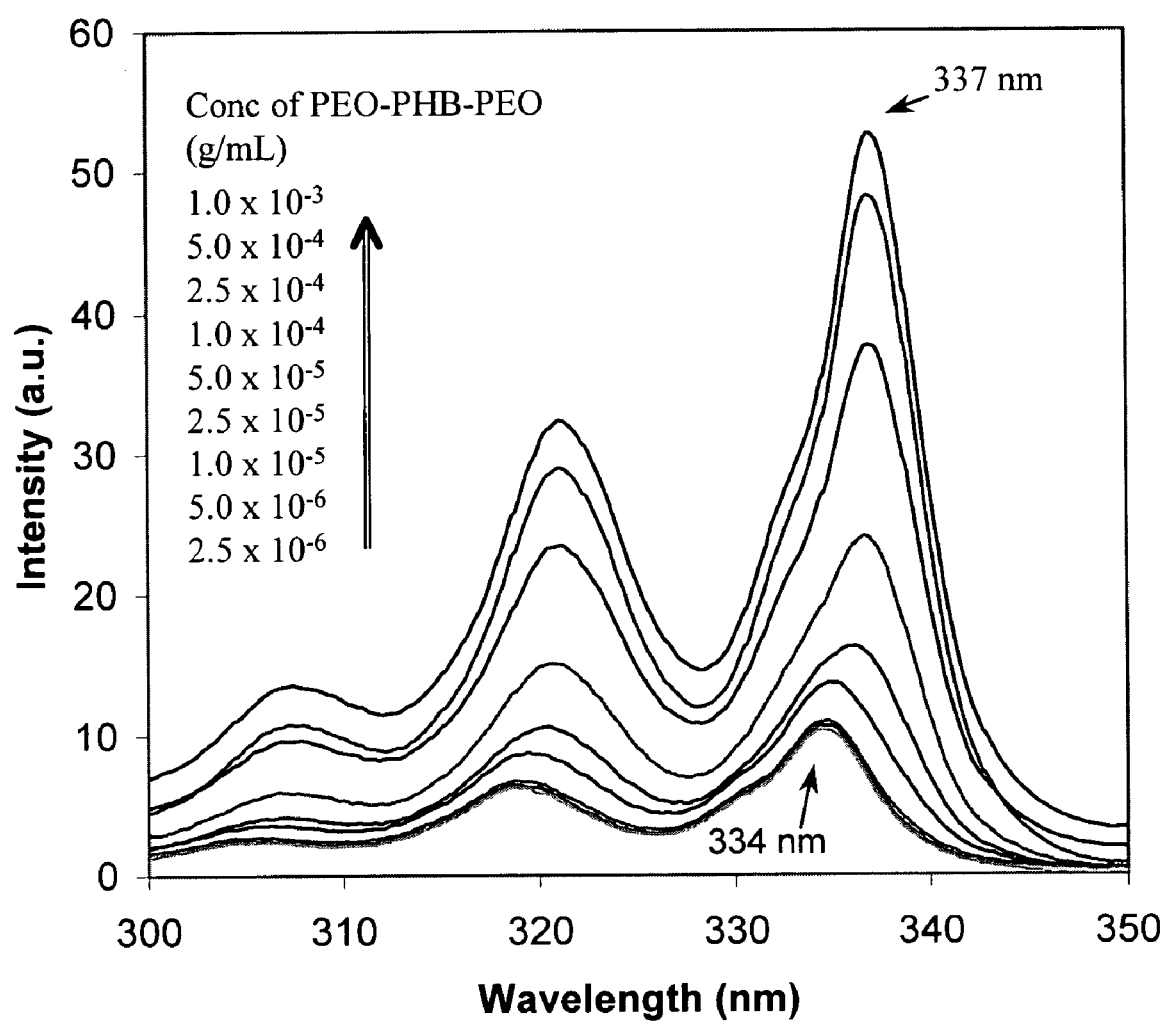
FIG. 21 provides a steady-state fluorescence excitation spectra monitored at 373 nm for a pyrene probe ($6.0\times10^{-7}$ M) in an aqueous solution of PEO-PHB-PEO copolymer from Example 5 at various concentrations at 23° C.
Figure 22:
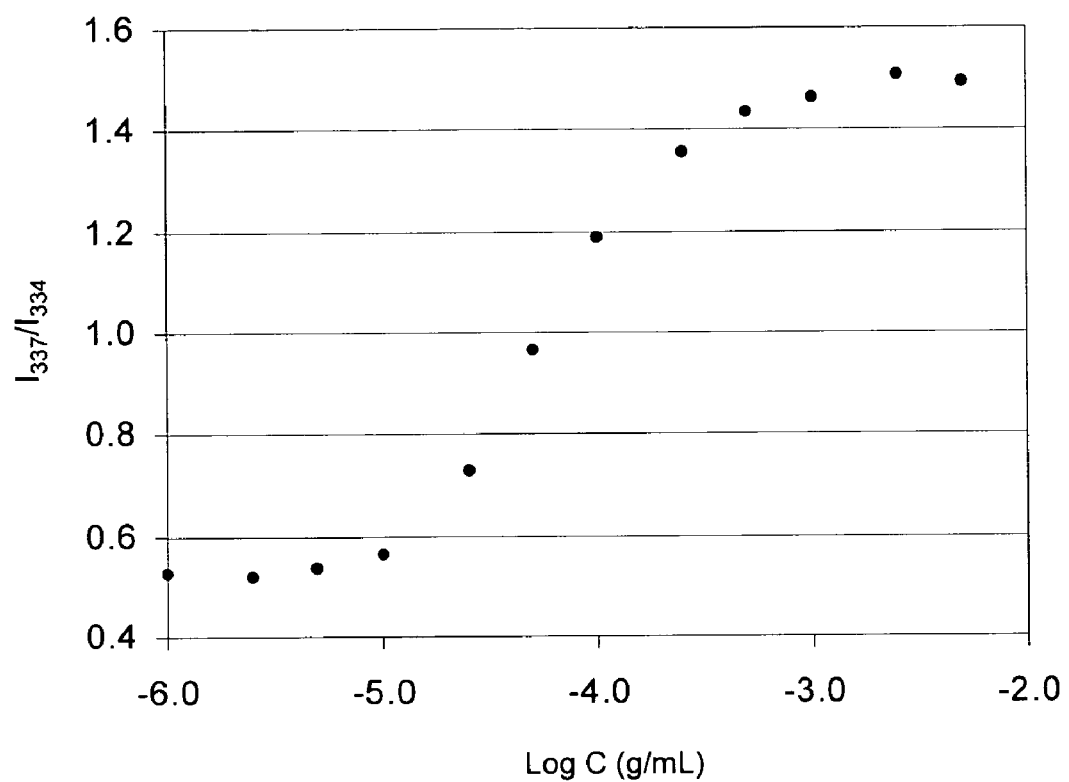
FIG. 22 illustrates the effect of concentration of the PEO-PHB-PEO copolymer from Example 5 on the $I_{337}/I_{334}$ ratio of pyrene in copolymer solutions at 23° C.

FIG. 21 shows the excitation spectra for pyrene in water at various concentrations of PEO-PHB-PEO copolymer. With increase in the copolymer concentration, a red shift of the 0-0 absorption band from 334 to 337 nm was observed. FIG. 22 shows the intensity ratio of $I_{337}/I_{334}$ of pyrene excitation spectra as a function of the logarithm of the copolymer concentrations. The $I_{337}/I_{334}$ vs. Log C plot presents a sigmoid curve. A negligible change of intensity ratio of $I_{337}/I_{334}$ was observed at low concentration range. With increase in the copolymer concentration, the intensity ratio exhibited a substantial increase at a certain concentration, reflecting the incorporation of pyrene into the hydrophobic core region of the micelles. Therefore, the cmc value was determined from the crossover point at the low concentration range in FIG. 22. The very low cmc value ($1.4 \times 10^{-5}$ g/mL) indicates a strong tendency of the triblock copolymer towards formation of micelles in aqueous environment.

Figure 23:
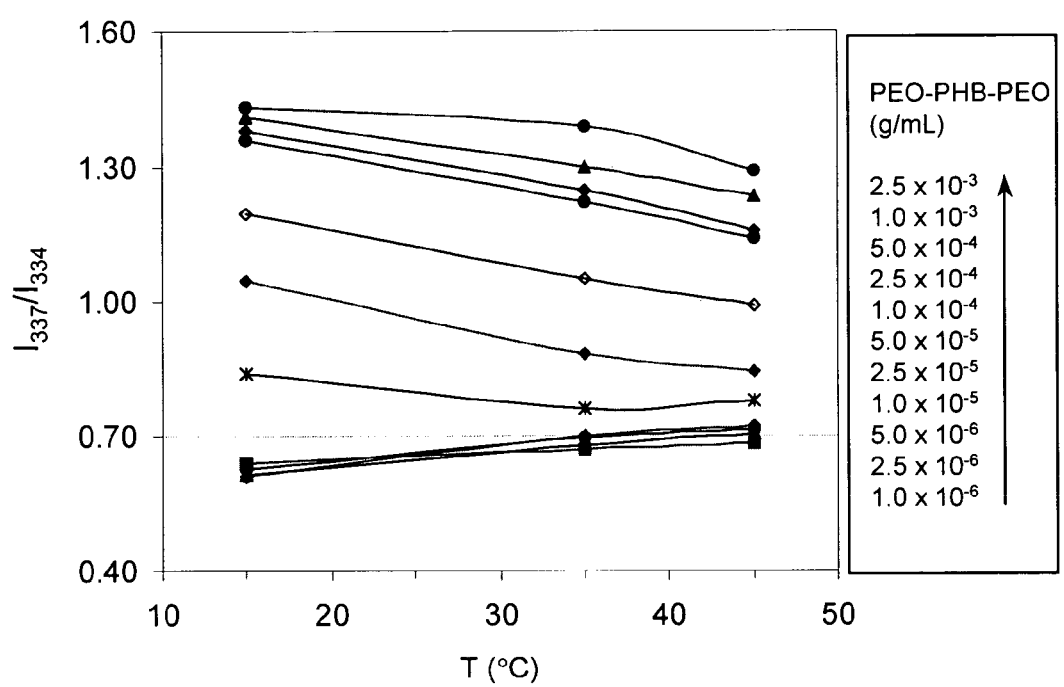
FIG. 23 illustrates the effect of temperature on $I_{337}/I_{334}$ ratio of pyrene in aqueous solutions of the PEO-PHB-PEO copolymer from Example 5 at different concentrations.

The formation of micelles was unexpectedly found to be relatively temperature-insensitive. As shown in FIG. 23, at temperatures ranging from 15 to 45° C., the $I_{337}/I_{334}$ ratio is primarily dependant on the copolymer concentration, rather than temperature. Therefore, the micelle formation of the PEO-PHB-PEO triblock copolymer is relatively temperature-insensitive. This is quite different from triblock copolymers having a middle poly($\alpha$-hydroxyalkanoic acid) and flanking PEO blocks consisting of PLLA or PGA, which are usually thermo-sensitive. Jeong (2002); Kissel (2002); Jeong (1997); Jeong (1999)) While not wishing to be limited by theory, the inventors believe that PHB has higher crystallinity and hydrophobicity than do poly($\alpha$-hydroxyalkanoic acids), thus the tendency of self-assembly of PHB segments in the block copolymers is much stronger and not dependent on the temperature change.

In summary, temperature-insensitive micelle formation of a novel biodegradable amphiphilic PEO-PHB-PEO triblock copolymer has been demonstrated. Although PHB has a related chemical structure to PLLA, the micelle behavior of PEO-PHB-PEO triblock copolymer is quite different from PEO-PLLA-PEO triblock copolymer. The micelles formed with the PEO-PHB-PEO triblock copolymer, which is difficult to dissociate at low temperature, and also not easy to aggregate to larger size at high temperature, are thus more stable and readily handled.

Example 6

In Vivo Tissue Biocompatability of α-CD-PEO-PHB-PEO Hydrogels

Hydrogel formed from α-CD and PEO-PHB-PEO (5000-2000-5000) in accordance with the procedure of Example 2 was injected intra-articularly into the knee joints of three rabbits. Phosphate Buffered Saline (PBS) was used as a negative control. The animals were sacrificed at 7 days after injection. The knee joints were harvested and examined by histology. The samples were evaluated under blinded conditions.

Figure 24A:
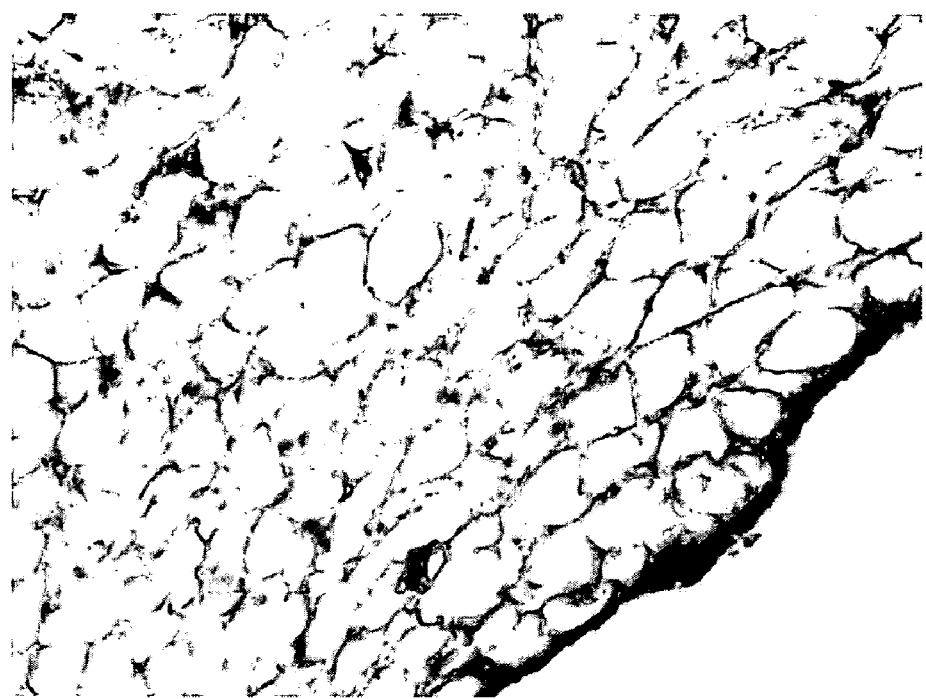
FIG. 24a provides an image (original magnification×10) showing the histology of the rabbit knee joint one week after intra-articular injection of phosphate buffered saline.
Figure 24B:
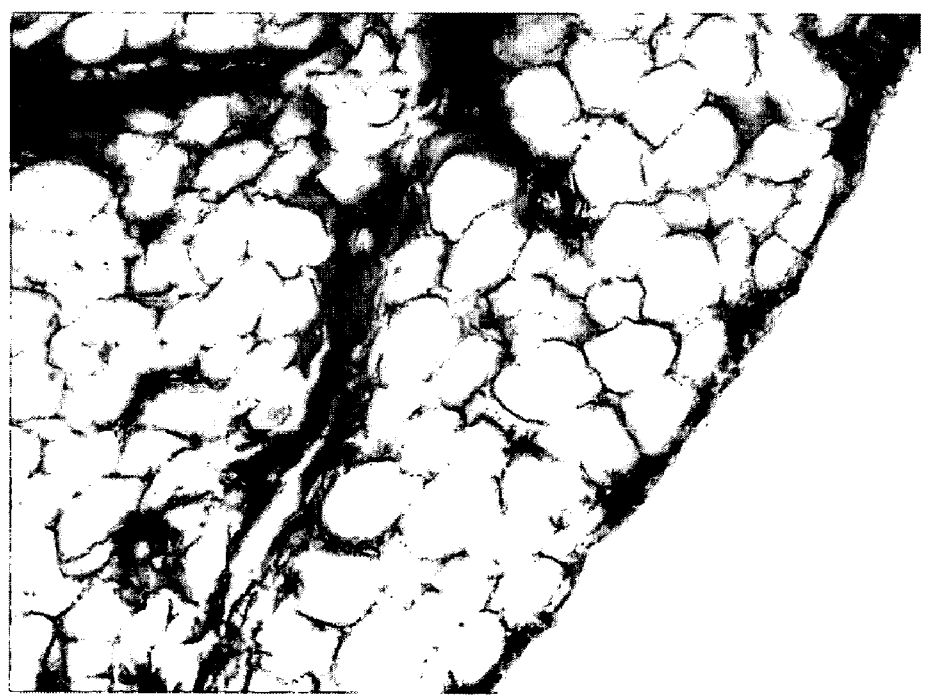
FIG. 24b provides an image (original magnification×10) showing the histology of the rabbit knee joint one week after intra-articular injection of an α-CD-PEO-PHB-PEO (5000-2000-5000) hydrogel.

The representative results of in vivo biocompatibility tests of the hydrogel in rabbit knee joints are shown in FIGS. 24a (PBS control) and 24b (α-CD-PEO-PHB-PEO Hydrogel). Although there was mild fibrosis in the synovium exposed to the 1-CD-PEO-PHB-PEO hydrogel shown in slide shown in FIG. 24b, there were no signification differences between these two samples. Overall analysis showed that there was no obviously inflammatory infiltrate in the joint synovium after injection of the hydrogel. The results showed biocompatibility of the hydrogel in the rabbit knee joint. There were no significant differences histologically and morphologically between the knees injected with hydrogel and PBS.

While the preferred embodiment of the invention has been illustrated and described, it will be appreciated that various changes can be made therein without departing from the spirit and scope of the invention.

The invention claimed is:

1. A drug delivery system, comprising:
   a hydrogel formed from an inclusion complex comprising cyclodextrin and an amphiphilic copolymer, wherein the copolymer includes an A polymer block comprising a poly(alkylene oxide) and a B polymer block comprising a poly(hydroxyalkanoate), wherein the poly(alkylene oxide) A block polymer is selected from the group consisting of poly(ethylene oxide), poly(tetramethylene oxide) and poly(tetrahydrofuran) and the poly(hydroxyalkanoate) B block polymer is selected from the group consisting of poly[(R)-3-hydroxybutyrate], poly[(R)-4-hydroxybutyrate], poly[(R)-3-hydroxyvalerate], poly[(R)-3-hydroxybutyrate]-co-Poly[(R)-3-hydroxyvalerate], poly[(R)-3-hydroxyhexanoate], Poly[(R)-3-hydroxyheptanoate], (S) enantiomers of each of such (R) enantiomers, racemic mixtures of such (S) and (R) enantiomers, and mixtures thereof; and
   a therapeutically effective amount of at least one therapeutic agent intimately contained within the hydrogel, wherein the copolymer is an amphiphilic triblock copolymer including a B polymer block mid-segment and two A polymer block end segments.

2. The system of claim 1, wherein the poly(alkylene oxide) A block polymer is poly(ethylene oxide).

3. A hydrogel comprising cyclodextrin and an amphiphilic copolymer in the form of an inclusion complex, wherein the copolymer includes an A polymer block comprising a poly(alkylene oxide) and a B polymer block comprising a poly(hydroxyalkanoate), wherein the copolymer is an amphiphilic triblock copolymer including a B polymer block mid-segment and two A polymer block end segments, wherein the poly(alkylene oxide) A block polymer is selected from the group consisting of poly(ethylene oxide), poly(tetramethylene oxide) and poly(tetrahydrofuran) and the poly(hydroxyalkanoate) B block polymer is selected from the group consisting of poly[(R)-3-hydroxybutyrate], poly[(R)-4-hydroxybutyrate], poly[(R)-3-hydroxyvalerate], poly[(R)-3-hydroxybutyrate]-co-Poly[(R)-3-hydroxyvalerate], poly[(R)-3-hydroxyhexanoate], Poly[(R)-3-hydroxyheptanoate], (S) enantiomers of each of such (R) enantiomers, racemic mixtures of such (S) and (R) enantiomers, and mixtures thereof.

4. The drug delivery system of claim 1, wherein the copolymer has a molecular weight of between 1,000 and 50,000.

5. The drug delivery system of claim 1, wherein the copolymer has a molecular weight of between 5,000 and 35,000.

6. The drug delivery system of claim 1, wherein the at least one therapeutic agent is selected from the group consisting of peptides, proteins, small molecules, genes, antigens, antibodies and fragments thereof and human recombinant proteins, DNA, RNA and DNA nanoparticles.

7. The drug delivery system of claim 1, wherein the at least one therapeutic agent is in a macromolecular form.

8. The drug delivery system of claim 1, wherein the at least one therapeutic agent is selected from the group consisting of analgesics, anesthetics, anti-arthritic drugs, disease modifying anti-rheumatic drugs, anti-asthma drugs, anticoagulants, anticonvulsants, antidepressants, antidiabetics, antineoplastics, antipsychotics, antihypertensives, antibiotics, antihistamines, decongestants, anti-inflammatories, muscle relaxants, anti-parasitic drugs, antiviral drugs, anti-restenotic agents, anti-spasm agents, chondroprotective agents, anti-adhesion agents, anti-tumor cell invasion agents, vasorelaxants, vasoconstrictors and immunosupressants.

9. The drug delivery system of claim 1, wherein the at least one therapeutic agent is selected from the group consisting of peptides, proteins including cytokines, growth factors, angiogenesis factors, soluble receptors, antibodies and fragments thereof and human recombinant proteins, small molecules, genes, antigens including vaccines, DNA, RNA and DNA nanoparticles.

* * * * *